US012653427B2

(12) United States Patent
Hurtz et al.

(10) Patent No.: US 12,653,427 B2
(45) Date of Patent: Jun. 16, 2026

(54) METHODS AND APPARATUS CONFIGURED TO TRANSMIT DATA IN CONTINUOUS ANALYTE MONITORS

(71) Applicant: Ascensia Diabetes Care Holdings AG, Basel (CH)

(72) Inventors: Robert W. Hurtz, Putnam Valley, NY (US); Igor Y. Gofman, Croton-on-Hudson, NY (US); Wei Dale Zhang, Dayton, NJ (US); Thomas A.J. Mayer, Jr., Glenmoore, PA (US); Ji Li, Wayne, NJ (US); Christopher A. Dionisio, Butler, NJ (US)

(73) Assignee: Ascensia Diabetes Care Holdings AG, Basel (CH)

( * ) Notice: Subject to any disclaimer, the term of this patent is extended or adjusted under 35 U.S.C. 154(b) by 133 days.

(21) Appl. No.: 17/334,103

(22) Filed: May 28, 2021

(65) Prior Publication Data

US 2021/0369152 A1     Dec. 2, 2021

Related U.S. Application Data

(60) Provisional application No. 63/033,825, filed on Jun. 2, 2020.

(51) Int. Cl.
A61B 5/145 (2006.01)
A61B 5/00 (2006.01)

(52) U.S. Cl.
CPC ...... *A61B 5/14532* (2013.01); *A61B 5/14503* (2013.01); *A61B 5/6801* (2013.01); *A61B 2562/12* (2013.01)

(58) Field of Classification Search
CPC ............ A61B 5/14532; A61B 5/14503; A61B 5/6801; A61B 2562/12; A61B 2560/0223;
(Continued)

(56) References Cited

U.S. PATENT DOCUMENTS

| | | | |
|---|---|---|---|
| 10,201,296 | B2 | 2/2019 | Sun et al. |
| 10,231,653 | B2 | 3/2019 | Bohm et al. |

(Continued)

FOREIGN PATENT DOCUMENTS

| | | | |
|---|---|---|---|
| CN | 106535765 A | | 3/2017 |
| JP | 2008246204 | | 10/2008 |

(Continued)

OTHER PUBLICATIONS

European Patent Application 21732817.8, Communication pursuant to Rules 161(1) and 162 EPC, issued Jan. 11, 2023.
(Continued)

*Primary Examiner* — Charles A Marmor, II
*Assistant Examiner* — Meghan R Kumar
(74) *Attorney, Agent, or Firm* — Erise IP, P.A.

(57) ABSTRACT

In one or more embodiments, a base unit of a wearable device for continuous analyte monitoring may include sensor memory circuitry and a sensor assembly. The sensor memory circuitry stores information (data) of at least one parameter of at least one component of the base unit, such as, e.g., the sensor assembly. The base unit is configured to couple to a transmitter unit of the wearable device and to transfer the information to the transmitter unit. Analyte determinations are made based at least in part on the information. Numerous other embodiments are provided.

23 Claims, 10 Drawing Sheets

(58) Field of Classification Search
CPC ... A61B 2562/18; A61B 5/0004; A61B 5/145;
A61B 5/14865
See application file for complete search history.

(56) References Cited

U.S. PATENT DOCUMENTS

| | | | |
|---|---|---|---|
| 2002/0042561 A1 | 4/2002 | Schulman et al. | |
| 2007/0135697 A1 | 6/2007 | Reggiardo | |
| 2007/0197889 A1* | 8/2007 | Brister | A61B 5/15142 |
| | | | 600/347 |
| 2011/0178378 A1* | 7/2011 | Brister | A61B 5/6833 |
| | | | 600/309 |
| 2011/0319734 A1 | 12/2011 | Gottlieb et al. | |
| 2012/0078071 A1 | 3/2012 | Bohm et al. | |
| 2012/0136610 A1 | 5/2012 | Fennell | |
| 2013/0245401 A1* | 9/2013 | Estes | A61B 5/7203 |
| | | | 600/309 |
| 2015/0286772 A1* | 10/2015 | Donnelly | G06F 30/367 |
| | | | 716/112 |
| 2016/0008029 A1 | 1/2016 | Brister et al. | |
| 2018/0000556 A1* | 1/2018 | Blair | A61F 13/44 |
| 2018/0368769 A1* | 12/2018 | Epstein | B32B 27/00 |
| 2019/0117133 A1 | 4/2019 | Halac et al. | |
| 2019/0274598 A1 | 9/2019 | Scott et al. | |
| 2019/0336055 A1* | 11/2019 | Shah | A61B 5/0002 |
| 2021/0137426 A1 | 5/2021 | Gofman | |

FOREIGN PATENT DOCUMENTS

| | | |
|---|---|---|
| JP | 2012516494 A | 7/2012 |
| JP | 2017504864 A | 2/2017 |
| WO | 2005015163 A2 | 2/2005 |

OTHER PUBLICATIONS

International Search Report and Written Opinion of International Application No. PCT/EP2021/064596 mailed Sep. 23, 2021.
Taiwanese Patent Application No. 110119942, Official Letter and Search Report, issued Aug. 19, 2024.
Japanese Patent Application 2022-534375, Office Action, issued Feb. 10, 2025.
European Patent Application 21732817.8 Office Action issued Jan. 10, 2025.
Japanese Patent Application 2022-534375, Office Action, issued Jul. 1, 2025.
Chinese Patent Application 202180007059.1 Notification to Grant Patent Right issued on Nov. 5, 2025.
Canadian Patent Application 3,179,267, Office Action, issued May 1, 2026.

* cited by examiner

502 — Assemble The Sensor Assembly Into The Baseplate

504 — Calibrate The Sensor Assembly

506 — Write Sensor Information To The Sensor Memory Circuitry

508 — Record Sensor Information Into A Manufacturing Database

510 — Seal And Package The Base Unit

512 — Sterilize The Base Unit

602 — Attach Base Unit And Insert Biosensor

604 — Couple The Transmitter Unit To The Base Unit

606 — Activate The Base Unit

608 — Read The Data Stored In The Sensor Memory Circuitry

610 — Has The Sensor Assembly Expired

612 — Generate Error Code

Yes

No

614 — Run Constant Analyte Monitoring For A Predetermined Period Of Time

600

*700*

Assembling A Sensor Assembly To A Baseplate ⟋ *702*

Assembling Sensor Memory Circuitry To The Baseplate ⟋ *704*

Determining At Least One Parameter Of At Least One Component Of The Base Unit ⟋ *706*

Storing Information Of The At Least One Parameter In The Sensor Memory Circuitry ⟋ *708*

Sterilizing The Base Unit ⟋ *710*

METHODS AND APPARATUS CONFIGURED TO TRANSMIT DATA IN CONTINUOUS ANALYTE MONITORS

CROSS REFERENCE TO RELATED APPLICATION

This claims the benefit of U.S. Provisional Patent Application No. 63/033,825, filed Jun. 2, 2020, the disclosure of which is hereby incorporated by reference herein in its entirety for all purposes.

FIELD

Embodiments of the present disclosure relate to continuous analyte monitoring methods and apparatus.

BACKGROUND

Continuous analyte monitoring in an in-vivo sample, such as continuous glucose monitoring (CGM), has become a routine monitoring operation, particularly in diabetes care. By providing real-time glucose concentrations, therapeutic actions may be applied in a more timely fashion and the glycemic condition may be better controlled.

During a CGM operation, a biosensor of a CGM apparatus is typically inserted subcutaneously and is continuously operated in an environment surrounded by tissue and interstitial fluid. The biosensor inserted under the skin provides a signal to a wireless CGM transmitter of the CGM apparatus that is indicative of the user's blood glucose level. These measurements may be made automatically many times throughout the day (e.g., every few minutes or at some other pre-established interval).

The wireless CGM transmitter may adhere to the outer surface of a user's skin, such as on the abdomen, or the back of the upper arm, while the biosensor is inserted through the skin so as to contact interstitial fluid. The biosensor interacts with the interstitial fluid, generating electrical signals that are proportional to the amount of glucose present. These electrical signals are communicated to the CGM transmitter for use in glucose value determinations.

Fabricating CGM assemblies of CGM transmitters and biosensors that are both comfortable for patients and cost effective remains a challenge. As such, improved CGM apparatus and CGM methods are desired.

SUMMARY

In some embodiments, a base unit of a wearable device for use during continuous analyte monitoring is provided. The base unit includes a sensor assembly including at least one biosensor configured to be located subcutaneously; and sensor memory circuitry configured to store information (data) related to at least one parameter of at least one component of the base unit, wherein the base unit is configured to be coupled to a transmitter unit of the wearable device, and wherein the information is transferable to the transmitter unit.

In some embodiments, a transmitter unit of a wearable device for use during continuous analyte monitoring is provided. The transmitter unit includes an electronic component configured to receive information (data) stored in a sensor memory circuitry of a base unit of the wearable device in response to the transmitter unit and the base unit being coupled together, wherein the information includes at least one parameter of at least one component of the base unit.

In some embodiments, a wearable device for use during continuous analyte monitoring is provided. The wearable device includes a base unit; a sensor assembly located in the base unit and configured to measure an analyte in interstitial fluid; sensor memory circuitry located in the base unit and configured to store information (data) of one or more parameters of one or more components in the base unit; and a transmitter unit configured to physically couple to the base unit, wherein the information is transferable from the sensor memory circuitry when the base unit and the transmitter unit are coupled together.

In some embodiments, a method of manufacturing a base unit of a constant analyte monitor is provided. The method includes assembling a sensor assembly to a baseplate; assembling sensor memory circuitry to the baseplate; determining one or more parameters of one or more components of the base unit; and storing information (data) of the one or more parameters in the sensor memory circuitry.

In some embodiments, a method of monitoring an analyte is provided. The method includes inserting a biosensor extending from a base unit of a wearable device into subcutaneous interstitial fluid; coupling the base unit and a transmitter unit of the wearable device together; transferring information (data) stored in sensor memory circuitry in the base unit to the transmitter unit, the information including at least one parameter of at least one component of the base unit; measuring a current passing through the biosensor; and determining an analyte concentration based at least in part on the current and the information.

Other features, aspects, and advantages of embodiments in accordance with the present disclosure will become more fully apparent from the following detailed description, the claims, and the accompanying drawings which illustrate a number of example embodiments. Various embodiments in accordance with the present disclosure may also be capable of other and different applications, and its several details may be modified in various respects, all without departing from the scope of the claims and their equivalents. Accordingly, the drawings and descriptions are to be regarded as illustrative in nature, and not as restrictive.

BRIEF DESCRIPTION OF THE DRAWINGS

The drawings, described below, are for illustrative purposes and are not necessarily drawn to scale. The drawings are not intended to limit the scope of the invention in any way. Accordingly, the drawings are to be regarded as illustrative in nature, and not as restrictive.

DETAILED DESCRIPTION

Figure 1A:
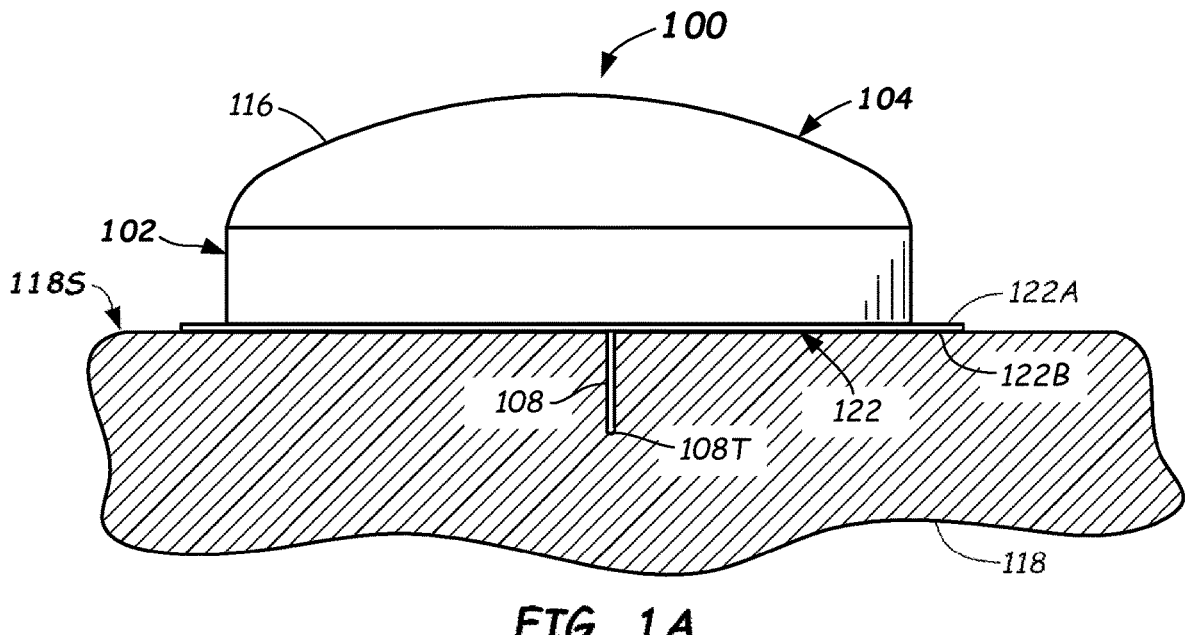
FIG. 1A illustrates a side elevation view of a wearable device, including a transmitter unit and a base unit, configured for use during continuous analyte monitoring in accordance with embodiments provided herein.

In order to monitor a person's analyte level more closely (e.g., glucose concentration) and detect changes in the analyte level, methods and apparatus for continuous analyte monitoring (e.g., continuous glucose monitoring (CGM)) have been developed. While CGM systems generate glucose signals "continuously" during operation, such as continuous electrochemical signals, measurements of the generated analyte (e.g., glucose) signals are typically performed every few minutes, rather than being truly continuous. The description below is related to continuous glucose monitoring, however, the apparatus and methods described below may be readily adapted to monitoring of other analytes in other continuous analyte monitoring systems, such as lactate for example.

CGM systems generally have a wearable portion (a "wearable device") that is worn on the body and that can communicate (e.g., wirelessly) with an external device, such as a hand-held receiver or another portable device, such as a smart phone with a suitable application software program (app). The wearable device may be worn for several days or even several weeks before being removed and replaced (e.g., 1-2 weeks). The wearable device includes a biosensor that is inserted (implanted) subcutaneously. The wearable device may also include analog circuitry coupled to the biosensor and configured to bias the biosensor and measure current signals generated by the implanted biosensor. The wearable device may also include processing circuitry for determining analyte (e.g., glucose) levels based on measured current signals, as well as electronic transmitter circuitry for communicating analyte (e.g., glucose) levels to an external receiving device. The wearable device may be attached (e.g., adhered) to the outer surface of the skin, such as to the abdomen, the back of the upper arm, or other suitable location. CGM systems measure analyte concentrations (e.g., glucose levels) in interstitial fluid or in samples of non-direct capillary blood.

CGM systems may provide frequent measurements of a user's analyte (e.g., glucose) levels without the need for each such measurement to be accompanied by the drawing of a blood sample, such as by finger sticks. CGM systems may still employ an occasional finger stick and the use of a blood glucose measuring (BGM) system, such as the Contour NEXT One® by Ascensia Diabetes Care AG of Basel Switzerland, for initiating calibration of the CGM system.

As described above, the wearable device of a CGM system is generally worn for up to two weeks, and then is removed and replaced with a new wearable device. Having to replace the wearable device of a CGM system every few weeks can significantly increase the costs of performing such continuous analyte monitoring. For example, according to aspects of this disclosure, the biosensor may need to be replaced, but the other components can be reused.

Embodiments provided herein provide a wearable device for use during continuous analyte (e.g., glucose) monitoring. The wearable device described herein includes a base unit (e.g., a disposable portion) and a transmitter unit (e.g., a reusable portion). The base unit may include a sensor assembly, including a biosensor configured to monitor a specific analyte, and sensor memory circuitry that electronically stores information (data) relevant to and/or unique to an individual base unit, such as to a biosensor assembly thereof. For example, the sensor memory circuitry may store at least one parameter of at least one component of the base unit. The sensor memory circuitry may include PROMs, EEPROMs, SRAMs, SDRAMs, and NOR and NAND flash memories, for example. Other types of sensor memory circuitry may be used.

In particular, the sensor memory circuitry may comprise a radiation hardened (rad-hard) memory, meaning that the sensor memory circuitry, and in particular, the rad-hard memory, will retain information (data) and will be functional even after being exposed to a dose of radiation, such as ionizing radiation (such as gamma (γ) radiation) and/or electron beam (E-beam) radiation that is high enough in a magnitude of the dose to sterilize the base unit. In some embodiments, the sensor memory circuitry may be placed in a rad-hard package. In some embodiments, a rad-hard package or rad-hard memory reduces the total ionizing dose (TID) received by the sensor memory circuitry relative to the TID environment exterior to the sensor memory circuitry. In some embodiments, the reduction of TID received by the sensor memory circuitry can be several orders of magnitude. The rad-hard sensory memory circuitry and/or the rad-hard package enables the sensor memory circuitry and/or the base unit to be sterilized by exposure to radiation without erasing or damaging the sensor memory of the sensor memory circuitry. Thus, a completed base unit may be placed in a container for shipment to a user. Then the base unit is sterilized using radiation without erasing or otherwise damaging the sensor memory circuitry.

The transmitter unit may include electronic circuitry used, for example, to provide a bias to the sensor assembly, measure current signals through the sensor assembly (or the biosensor associated therewith), compute analyte concentration values (e.g., glucose concentration values) based on the measured current signals, and transmit the analyte concentration values and/or related information to an external device, such as an external receiver device or an external transceiver device. In some embodiments, the raw readings and/or data generated by the biosensor may be transmitted and then analyte concentration values may be computed by the external device.

Example circuitry within the transmitter unit may include an analog front end configured to bias the sensor assembly and to sense current passing through the sensor assembly at suitable time increments. The circuitry may include operational amplifiers, current sources, current sensing circuitry, comparators, etc. Other circuitry and components within the transmitter unit may include processing circuitry such as analog-to-digital converters for digitizing current signals, memory for storing digitized current signals, a controller such as microprocessor, microcontroller, or the like configured to compute analyte concentration levels based on measured current signals, and transmitter circuitry for transmitting analyte concentration levels to the external device.

The transmitter unit may also include circuitry and/or components that cause the sensor memory circuitry in the base unit to transmit information (e.g., data) stored therein and circuitry and/or components that receive the information. The information may be data that is stored and transmitted by data storage and transmission techniques. For example, when the transmitter unit and the base unit are physically coupled together, the transmitter unit and the base unit may become electrically coupled. The electrical coupling may cause the information stored in the sensor memory circuitry to be transmitted to the transmitter unit. The information may be used by the circuitry in the transmitter unit and/or the external receiver device to calculate analyte concentrations and for other functions, such as data display (e.g., display of analyte concentration values and/or trends).

Electronic circuitry is generally the most expensive portion of the wearable device and, as designed, can last significantly longer than the period in which the wearable devices are employed. The base unit includes components, such as a biosensor, that penetrates skin and needs to be frequently replaced. For example, wearable devices are typically discarded after about two weeks, while the circuitry within the transmitter units may last indefinitely in some cases. In some embodiments, the reusable transmitter unit may be reused with 2 or more, 3 or more, 4 or more, 5 or more, 10 or more, 20 or more, 30 or more, 40 or more, 50 or more, or even 100 or more, base unit replacements.

In some embodiments, a wearable device for use during continuous analyte monitoring may include a base unit (e.g., a disposable base unit) containing at least a sensor assembly and sensor memory circuitry. The wearable device may also include a reusable transmitter unit configured to interface with the base unit and receive information stored in the sensor memory circuitry of the base unit. In some embodiments, the base unit may be configured to be disposed of after a single analyte monitoring period (e.g., 10-14 days), and the transmitter unit may be configured to be detached from the base unit after the single analyte monitoring period and re-used in (e.g., reattached to) another new base unit. These and other embodiments, as well as methods for manufacturing and/or using such a wearable device, are described below with reference to FIGS. 1A-8.

Reference is now made to FIGS. 1A-1D, which illustrate various views of a wearable device 100 (e.g., continuous analyte monitor) for use during continuous analyte monitoring (e.g., continuous glucose monitoring) in accordance with one or more embodiments provided herein. The wearable device 100 is illustrated as being at least partially dome shaped, at least on a portion thereof. The wearable device 100 is not limited to the dome shape illustrated herein and may have other shapes. A base unit 102 and a transmitter unit 104 may be any suitable shape in top plan view (e.g., round, oval, square, rectangular, or the like). For example, the wearable device 100 may have a primarily rectangular shape and may be sized and shaped to resemble a medical bandage. In such embodiments, the base unit 102 may be rectangular in plan view.

Figure 1B:
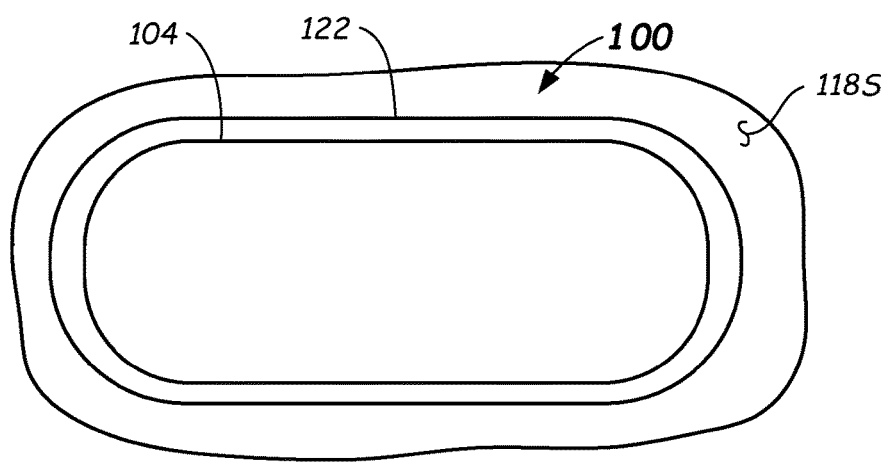
FIG. 1B illustrates a top plan view of the wearable device of FIG. 1A in accordance with one or more embodiments provided herein.

The base unit 102 may be a disposable unit and the transmitter unit 104 may be a reusable unit, wherein the transmitter unit 104 and the base unit 102 are configured to be coupled together. In some embodiments, the base unit 102 and the transmitter unit 104 are also configured to be detachable from one another. For example, the transmitter unit 104 and the base unit 102 may physically couple together to form the wearable device 100 as illustrated in FIGS. 1A and 1B. Any suitable mechanical mechanism configured to allow coupling of the transmitter unit 104 to the base unit 102 may be used. When physically coupled, the transmitter unit 104 and the base unit 102 may also electrically couple together so that data signals and/or electric current may be communicated and passed between electrical components in the transmitter unit 104 and in the base unit 102. This communication may be in response to the transmitter unit 104 and the base unit 102 being physically coupled together in some embodiments. In other embodiments, communication may be initiated by a command, such as a start command or the like.

Both the transmitter unit 104 and the base unit 102 may be sealed units (e.g., waterproof), with only electrical contacts of the transmitter unit 104 and the base unit 102 exposed as described below. Once the transmitter unit 104 and the base unit 102 are physically coupled together, the electrical contacts may also be sealed from the external environment, such as by the use of a sealing member.

A biosensor 108 (e.g., a portion inserted through the user's skin 118) may extend from the base unit 102 and may be configured to be at least partially located in interstitial fluid in a subcutaneous region as described herein. The biosensor 108 may be or may include an analyte sensor or an analyte sensor portion, such as at or near the tip 108T. The biosensor 108 may be inserted with an insertion device (not shown) having a sharpened tip that pierces skin to introduce the biosensor 108 into a subcutaneous region of a user. Any suitable inserter device may be used. The sensor circuitry coupled to the biosensor 108 may include devices that apply at least one bias voltage to the analyte sensor portion of the biosensor 108 within the interstitial fluid wherein other devices measure the resulting current flow, which is proportional to the analyte being monitored.

In some embodiments, the base unit 102 is configured to be disposed of after a single analyte monitoring period (e.g., 7 days, 10 days, 14 days, or some other suitable time period). In some embodiments, the transmitter unit 104 may be configured to be removed (detached) from the base unit 102 after the single analyte monitoring period and re-used with another new base unit.

Figure 1C:
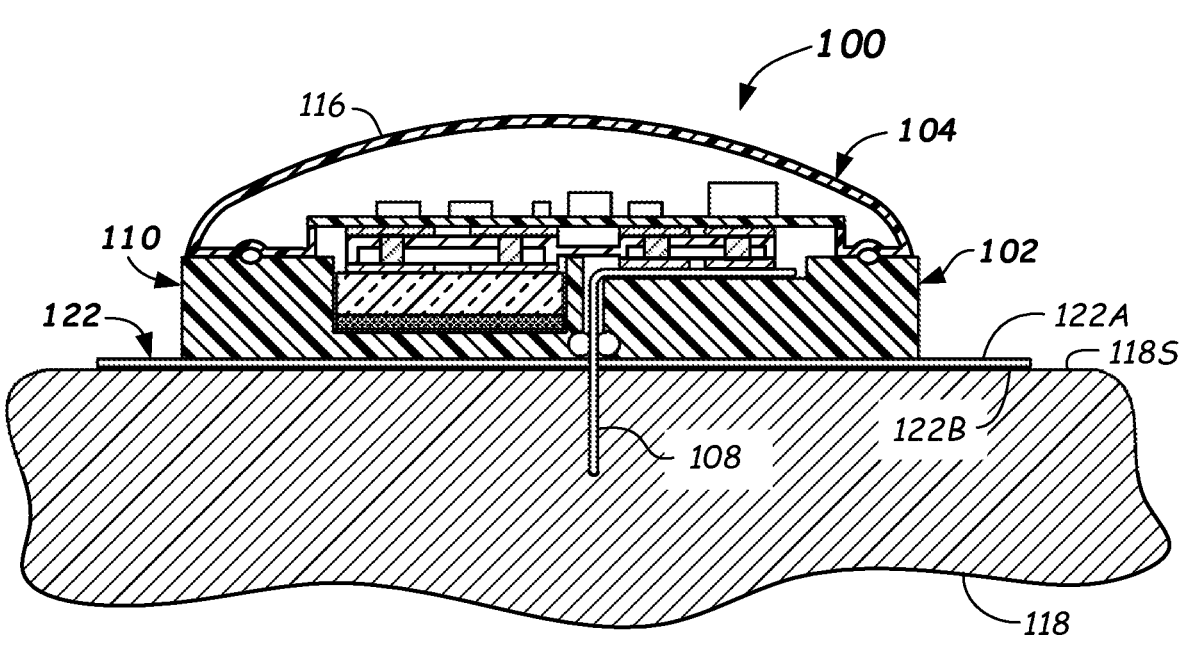
FIG. 1C illustrates a cross-sectioned, side elevation view of the wearable device of FIG. 1A including a base unit and a transmitter unit in accordance with one or more embodiments provided herein.
Figure 1D:
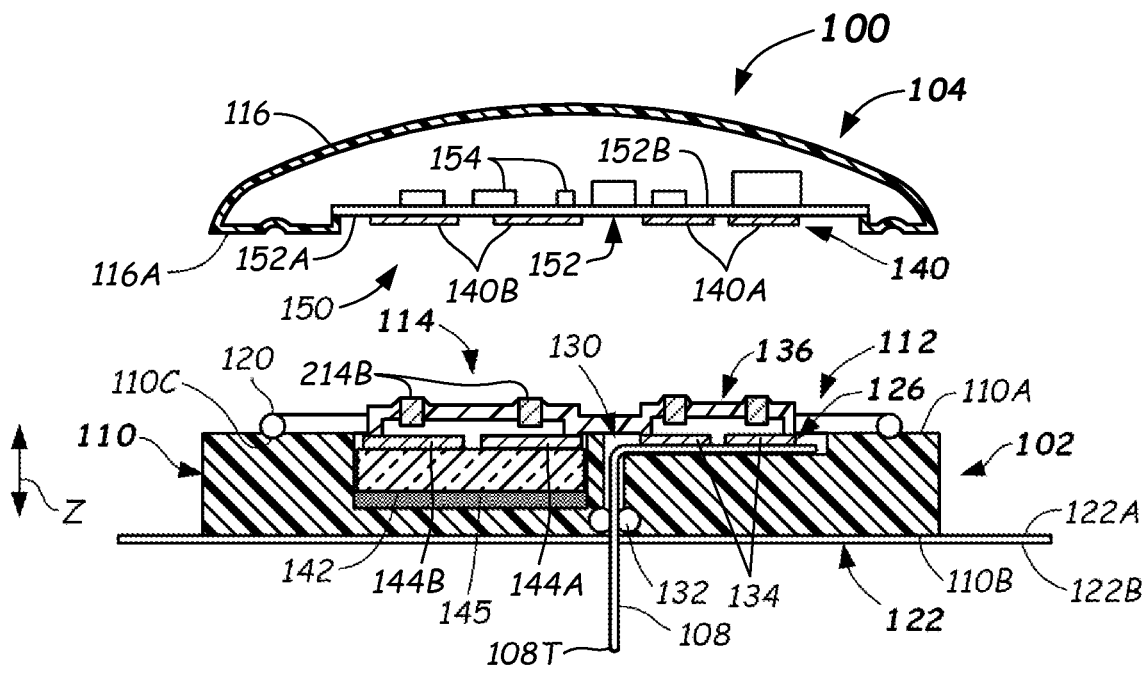
FIG. 1D illustrates a cross-sectioned, side exploded view of the wearable device of FIG. 1C with the transmitter unit separated from the base unit in accordance with one or more embodiments provided herein.

As shown in FIGS. 1C and 1D, the base unit 102 may include a baseplate 110 having a sensor assembly support location 112 and a memory circuitry location 114. The baseplate 110 may have a first surface 110A and an opposing second surface 110B. The first surface 110A may be configured to abut or be located adjacent a corresponding surface 116A of the transmitter unit 104. The second surface 110B may be configured to be located adjacent and/or be interconnected to the skin surface 118S (FIG. 1A) of a user. The first surface 110A may include a recessed portion 110C, such as a groove, that is configured to receive a gasket 120, such as an O-ring. For example, the recessed portion 110C may be a perimeter groove or the like that receives the gasket 120 to seal the periphery between the transmitter unit 104 and the base unit 102. In some embodiments, the baseplate 110 may be formed from a plastic, such as, but not limited to, acrylonitrile butadiene styrene (ABS), polycarbonate, nylon, acetal, polyphthalamide (PPA), polysulfone, polyethersulfone, polyetheretherketone (PEEK), polypropylene, high-density polyethylene (HDPE), and low-density polyethelene (LDPE). Other suitable materials may be used in the baseplate 110.

An adhesive layer 122, such as a double-sided tape or pressure sensitive adhesive, may be attached (e.g., adhered) to the second surface 110B of the baseplate 110 and may adhere the base unit 102 to the skin surface 118S of the user. The adhesive layer 122 can include a first side 122A and a second side 122B located opposite the first side 122A. The first side 122A may adhere to the second surface 110B of the baseplate 110. The second side 122B of the adhesive layer 122 may be configured to adhere to the skin surface 118S of the user, so as to adhere the base unit 102 to the skin surface 118S.

Figures 2A, 2B:
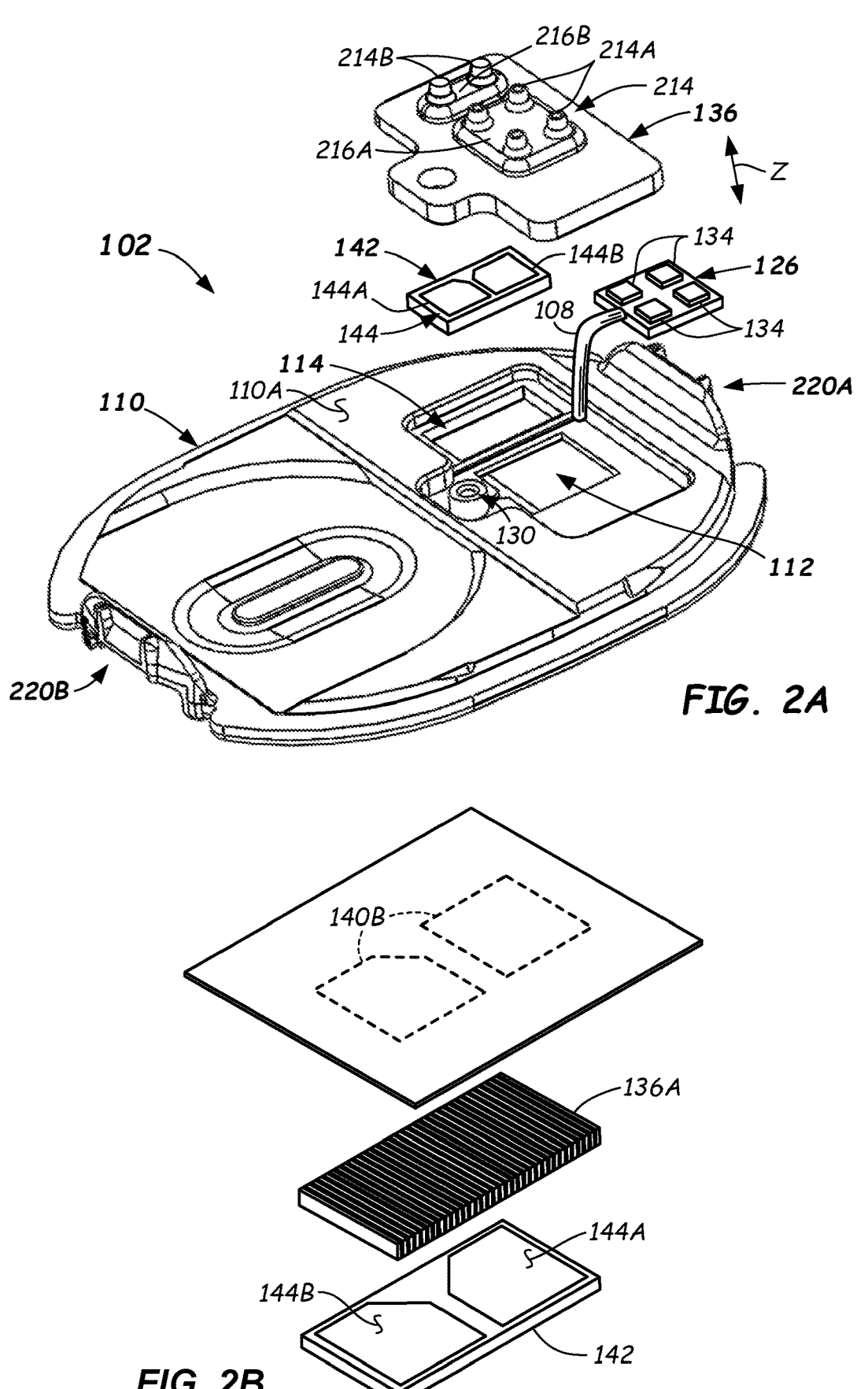
FIG. 2A illustrates an exploded, perspective view of a base unit of a wearable device in accordance with one or more embodiments provided herein.
FIG. 2B illustrates an exploded, perspective view of sensor memory circuitry, a conductor, and a printed circuit board of the wearable device of FIG. 2A in accordance with embodiments provided herein.

Additional reference is made to FIG. 2A, which illustrates an exploded, isometric view of an embodiment of the base unit 102. The sensor assembly support location 112 may provide a support location for a sensor assembly 126 that is used to measure or sense an analyte in subcutaneous tissue, such as in interstitial fluid, of the user. For example, the sensor assembly 126 may be configured to measure an analyte (e.g., glucose) in subcutaneous tissue. The sensor assembly support location 112 may be any suitable shape (e.g., rectangular, square, round, etc.) that supports and/or retains the sensor assembly 126 within or to the base unit 102. The sensor assembly 126 may be electrically and physically coupled to the biosensor 108. In some embodiments, the sensor assembly 126 may be integrally formed with the biosensor 108. The sensor assembly 126 may facilitate conducting electric signals to and from the tip 108T of the biosensor 108 and/or other portions of the biosensor 108.

The biosensor 108 may include an active region including one or more catalytic agents and/or reagents configured to sense the presence and concentration levels of a particular analyte, such as glucose. The baseplate 110 may include a bore 130 through which the biosensor 108 may pass. A gasket 132 (e.g., an O-ring—See also FIGS. 1C and 1D) may be located at least partially within the bore 130 and may prevent contaminants from passing through the bore 130 after insertion of the biosensor 108. For example, the gasket 132 may form a seal between the biosensor 108 and the bore 130 to prevent contaminants (e.g., blood) from entering the base unit 102. The gasket 132 may also prevent other contaminants from contacting the skin surface 118S of the user.

The sensor assembly 126 may include a plurality of electrically conductive contact pads 134 that electrically couple the sensor assembly 126 to other components and ultimately to the transmitter unit 104. In the embodiments described herein, the sensor assembly 126 includes four contact pads 134. In other embodiments, the sensor assembly 126 may include more or fewer contact pads 134.

A connector 136 may be electrically coupled to (e.g., contacting) the contact pads 134 and may electrically couple the contact pads 134 to sensor pads 140A of the transmitter unit 104. In some embodiments, the connector 136 may be an elastomeric connector, which may be referred to as a zebra strip. In some embodiments, the connector 136 may be a dotted connector or a dotted elastomeric connector. In some embodiments, the connector 136 may conduct solely in a z-direction, such as along a z-axis (FIG. 1D). Thus, the connector 136 may be a single device that may be placed over all the contact pads 134 and conducts current solely to locations directly above the contact pads 134. In such embodiments, the connector 136 may electrically couple the contact pads 134 to the sensor pads 140A of the transmitter unit 104 when the transmitter unit 104 and the base unit 102 are physically coupled together.

The base unit 102 includes sensor memory circuitry 142 that may be packaged as a memory device. In some embodiments, the memory circuitry and/or the memory device may be a single memory component. The sensor memory circuitry 142 may be secured within the memory circuitry location 114 by an adhesive 145, such as a double-sided tape or an epoxy adhesive, for example. Other securing configurations may be used to secure the sensor memory circuitry 142 within the memory circuitry location 114 or to another location within the base unit 102. The sensor memory circuitry 142 may include a radiation hardened memory (rad-hard memory) or may be located within a rad-hard package. A rad-hard memory includes a package and/or circuitry that retains information (e.g., data) stored therein when the package and/or the circuitry is exposed to radiation used to sterilize the base unit 102. The sensor memory circuitry 142 may include a programmable read-only memory (PROM), an electrically erasable programmable read-only memory (EEPROM), a static random access memory (SRAM), synchronous dynamic random-access memory (SDRAM), and/or NOR and NAND flash memories. Other types of sensor memory circuitry may be used for the sensor memory circuitry 142.

During manufacturing of the base unit 102 and/or the wearable device 100, the base unit 102 and/or the wearable device 100 may be sterilized using radiation, such as ionizing radiation, gamma (γ) radiation, and/or electron beam (E-beam) radiation. In some embodiments, the base unit 102 is manufactured separate from the transmitter unit 104, so just the base unit 102 is sterilized using radiation. In some embodiments, the transmitter unit 104 may not be sterilized using radiation. For example, the base unit 102 may be exposed to radiation to sterilize all the components therein.

Conventional memory devices and other electronic components may be damaged by the radiation used during sterilization. For example, components within conventional memory devices may be damaged or the conventional memory may be erased by the radiation. The sensor memory circuitry 142 may be rad-hard and/or packaged in a rad-hard package. A rad-hard sensor memory circuitry 142 or sensor memory circuitry packaged in a rad-hard package provides that the sensor memory circuitry 142 may be exposed to a total ionizing dose (TID) of radiation used for sterilization without information (data) stored therein being erased.

In some embodiments, a radiation hardened (rad-hard) package or rad-hard memory reduces the total ionizing dose (TID) received by the sensor memory circuitry 142 in the package relative to the total ionizing dose environment exterior to the package. In some embodiments, the reduction of TID is several orders of magnitude. The rad-hard sensor memory circuitry 142 enables the sensor memory circuitry 142 and the base unit 102 to be sterilized using radiation without erasing and/or damaging the sensor memory circuitry 142. For example, the base unit 102 may be assembled with the sensor memory circuitry 142 affixed therein. The base unit 102 with the sensor memory circuitry 142 affixed therein may then be sterilized using radiation.

In some embodiments, the sensor memory circuitry 142 may have a one-wire interface, which utilizes a voltage-based digital system that works with only two contacts, data and ground, for half-duplex bidirectional communication. Reference is made to FIG. 2B, which illustrates an exploded view of an embodiment of the sensor memory circuitry 142 and a portion of an alternative connector 136A. The embodiment of the sensor memory circuitry 142 has two contacts (e.g., two external nodes), which are a data contact pad 144A (e.g., a data node) and a ground contact pad 144B (e.g., a ground node). In some embodiments, these two contacts are the only contact pads or external nodes of the sensor memory circuitry 142. The one-wire type sensor memory circuitry 142 may be implemented for use in a momentary contact environment. For example, either disconnecting voltage from the sensor memory circuitry 142 or a loss of voltage to a power source puts the sensor memory circuitry 142 into a defined reset state. When the voltage returns to the sensor memory circuitry 142, the sensor memory circuitry 142 wakes up and may signal its presence. As described below, the sensor memory circuitry 142 may then transmit information stored therein, such as to the transmitter unit 104. Other types of memory circuitry may be used in the sensor memory circuitry 142. For example, the sensor memory circuitry 142 may include inter-integrated circuit (I2C) or serial peripheral interface (SPI) architectures.

The connector 136A may be used in place of the connector 136. The connector 136A may be an elastomeric connector, such as a z-connector, having repeating layers of conductors and insulators. Accordingly, the connector 136A conducts in the z-direction as described above.

Each sensor memory circuitry may store sensor information that is specific to individual base units and/or components therein. For example, each sensor memory circuitry may store at least one parameter of at least one component of a base unit in which it is located. Thus, the sensor memory circuitry 142 may store information that is specific to the base unit 102 and/or at least one component therein. The sensor information may include one or more parameters including:

a. Electrode Sensitivity Slope
    b. Manufacturing Date
    c. Batch or Lot number
    d. Security Code
    e. EEPROM Version
    f. Serial Number Sensitivity information may include sensitivity slope of the electrode of the biosensor 108 and/or the sensor assembly 126. In embodiments where the base unit 102 includes more than one biosensor, the sensitivity information may include data, such as sensitivity slopes of each of the biosensors.

The sensitivity information may include one or more mathematical functions or coefficients, for example, which may be obtained by testing the sensor assembly 126. Each biosensor and/or sensor assembly may be unique with regard to at least their respective sensitivities, so the information may include unique parameters related to the biosensor 108 and/or the sensor assembly 126 located in the same base unit 102. The transmitter unit 104 or other component that processes data generated by the sensor assembly 126 may use the sensitivity information or parameters related to other components to correctly calculate and determine analyte levels.

In some embodiments, one or more parameters (e.g., sensor information) may include a manufacturing date of one or more components in the base unit 102. For example, the sensor information may include the date of manufacture of the sensor assembly 126, the biosensor 108, and/or the sensor memory circuitry 142. The sensor information may be used to determine if a component within the base unit 102 is out of date. For example, some components within the base unit 102 may have a limited shelf life. If the base unit 102 is attempted to be used and has one or more components with an expired shelf life, an indication may be provided to the user. In some embodiments, the sensor information may include the manufacture date of the biosensor 108 or plurality of biosensors if the base unit 102 includes more than one biosensor. Devices analyzing analyte levels determined by the biosensor 108 may provide an indication if the age of the biosensor 108 is greater than a predetermined age.

In some embodiments, the sensor information may include at least one unique identifier of one or more components of the base unit 102, which may distinguish (e.g., identify) the base unit 102 and/or components thereof from other base units. The at least one unique identifier may be a serial number and/or a lot number, for example. In some embodiments, the unique identifier may include a serial number and/or a lot number of the base unit 102, the sensor assembly 126, the sensor memory circuitry 142, and/or one or more other components of the base unit 102. Devices analyzing analyte levels may use the one or more unique identifiers to determine if any components have been recalled or have been identified as being possibly defective, for example. The devices may also base analyte calculations or determinations on the actual components in the base unit 102 and/or the base unit 102 as determined by their unique identifiers.

In some embodiments, the sensor information may include one or more model numbers or other identifications of components within the base unit 102 or identification of the base unit 102. In some embodiments, the sensor information may include a model of the sensor memory circuitry 142, the sensor assembly 126, the base unit 102, and/or other components of the base unit 102. The model numbers and/or generic identification may be used when processing data generated by the base unit 102. For example, a certain model of the biosensor 108 may have different parameters than another model of biosensor.

In some embodiments, the sensor information may include one or more security codes used to access components of the base unit 102 or the transmitter unit 104. For example, the transmitter unit 104 or another component that processes data generated by the base unit 102 may require the security code stored within the sensor memory circuitry 142 to allow communication therewith. The use of the security code may prevent bootleg or unauthorized base units from communicating with the transmitter unit 104 or other devices. Accordingly, the security codes may prevent the wearable device 100 from reporting possibly erroneous analyte levels due to the use of improper base units, or otherwise improve security.

During manufacture and/or assembly of the base unit 102, the sensor assembly 126 may be placed into the sensor assembly support location 112 and the sensor memory circuitry 142 may be placed into the memory circuitry location 114. The above-described sensor information may be programmed into the sensor memory circuitry 142 before or after the sensor memory circuitry 142 is placed within the base unit 102 as described further below.

In some embodiments, the connector 136 may include one or more electrodes 214 that may be electrically coupled to at least some components within the base unit 102 and the transmitter unit 104 (FIGS. 1A-1D). The electrodes 214 may be axially (in Z direction) moveable in the body of the connector 136 and may be biased relative to the connector 136 in order to make electrical contact with components (e.g., contact pads) within the base unit 102 and/or the transmitter unit 104. In some embodiments, the number of electrodes 214 may be equal to the number of contact pads on components within the base unit 102 and/or the transmitter unit 104. In the example of FIGS. 2A and 2B, the sensor assembly 126 can include four contact pads 134 and the sensor memory circuitry 142 can include two contact pads 144, a data contact pad 144A and a ground contact pad 144B (e.g., nodes), so the connector 136 includes six electrodes 214 formed therein.

One or more of the electrodes 214 may be located in planes, which may group the electrodes according to the electrical components the electrodes 214 are configured to contact and allow them to be biased together. For example, four sensor electrodes 214A may be configured to electrically contact the plate-like sensor pads 140A on the transmitter unit 104 and the four sensor electrodes 214A may also contact the four contact pads 134 of the sensor assembly 126. Likewise, two memory electrodes 214B of the connector 136 may be configured to contact the two contact pads 144 of the sensor memory circuitry 142 and the memory pads 140B of the transmitter unit 104.

Thus, the contact pads 140 include sensor pads 140A that electrically couple to the sensor assembly 126 by way of sensor electrodes 214A when the transmitter unit 104 and the base unit are physically coupled together, i.e., by biasing (downward as shown in FIG. 1D) sensor electrodes 214A into contact with the contact pads 134. Likewise, the contact pads 140 may include memory pads 140B that electrically couple to the sensor memory circuitry 142 by way of the memory electrodes 214B when the transmitter unit 104 and the base unit 102 are physically coupled together, by biasing (downward as shown in FIG. 1D) sensor electrodes 214A into contact with the contact pads 144. The sensor pads 140A may be electrically coupled to one or more components within the transmitter unit 104 that receive data and/or process data from the sensor assembly 126 and/or transmit signals, including bias voltages and currents, to the sensor assembly 126. The memory pads 140B may electrically couple to one or more components within the transmitter unit 104 that transmit signals to, and/or receive signals from, the sensor memory circuitry 142.

The embodiment of the connector 136 of FIG. 2A may include a sensor plate 216A and a memory plate 216B. The sensor plate 216A may include the sensor electrodes 214A and the memory plate 216B may include the memory electrodes 214B. The connector 136 may include other plates and/or other electrodes.

The wearable device 100 (FIGS. 1A-1D) may include a power source (not shown in FIGS. 1A-2B), such as a battery (312—FIGS. 3, and 4A-4B), that is configured to provide power to components of the wearable device 100. In some embodiments the power source may be a battery, a storage capacitor, a solar cell, a generator, or the like. In some embodiments, the power source may provide power to the sensor memory circuitry 142 when the transmitter unit 104 and the base unit 102 are physically coupled together. In some embodiments, the power source may be located in the base unit 102 and in other embodiments the power source may be located in the transmitter unit 104. In some embodiments, at least one of the sensor assembly 126 and the sensor memory circuitry 142 is configured to receive power in response to the coupling of the transmitter unit 104 to the base unit 102. In embodiments wherein the power source has a long life, the power source may be located in the transmitter unit 104. In embodiments wherein the power source has a short life, the power source may be located in the base unit 102 since the base unit 102 also has a short life span and both can then be replaced concurrently. In some embodiments, the transmitter unit 104 and the base unit 102 may each have a power source.

The transmitter unit 104 may include one or more electronic components that communicate with one or more electronic components within the base unit 102 and with one or more external devices. Referring again to FIGS. 1A-1D, the transmitter unit 104 may include an encapsulation layer 116 (e.g., a top cover) that may be configured to be located against or over the base unit 102. The encapsulation layer 116 may include an opening 150 that may be configured to receive at least a portion of the base unit 102. The encapsulation layer 116 may encapsulate electronic and other components within the transmitter unit 104 to prevent the components from being exposed to contaminants. In some embodiments, the encapsulation layer 116 may be a pre-molded base into which a substrate 152 is positioned prior to formation of encapsulation layer 116 (e.g., by a molding process).

As described below, the substrate 152 may support components, such as electrical components and contact pads 140, located within or on the transmitter unit 104. In some embodiments, the substrate 152 may be a printed circuit board, such as a flexible printed circuit board, and may be employed to support electronic components, such as an analog front-end circuit and a transmitter module as described herein. The substrate 152 may be fabricated from materials such copper, kapton, polyester (PET), polyethylene naphthalate (PEN), polymides, fiberglass and acrylic adhesives. The substrate 152 may be made of other materials.

In some embodiments, the encapsulation layer 116 may be formed from a single layer or multiple layers. For example, the encapsulation layer 116 may be formed from one or more layers of liquid silicone rubber (LSR), a thermoplastic elastomer (TPE), or the like. Other materials may be used such as, but not limited to, ABS, polycarbonate, nylon, acetal, PPA, polysulfone, polyethersulfone, PEEK, polypropylene, HDPE, LDPE, etc. Other materials may be used. In some embodiments, the encapsulation layer 116 may be formed at a temperature of less than 100° C., and in some embodiments at a temperature of less than 80° C.

In the embodiments of FIGS. 1A-1D, the substrate 152 may be located in the opening 150 or at least partially accessible via the opening 150. The memory pads 140B and the sensor pads 140A may be attached to a lower surface 152A of the substrate 152 and may be accessible via the opening 150. One or more electronic components 154 may be physically and/or electrically coupled to an upper surface 152B of the substrate 152.

The transmitter unit 104 and the base unit 102 may be configured to be coupled together to complete the wearable device 100. For example, the transmitter unit 104 may be configured to be attached to, detached from, inserted in and/or removed from the base unit 102. Various retention features may be included in the base unit 102 and the transmitter unit 104 for such coupling. The retention features may enable the transmitter unit 104 to be removably attached to the base unit 102, i.e., it may be detachable.

Referring to FIG. 2A, the base unit 102 may include a first retention feature 220A and a second retention feature 220B that mechanically couple to and/or interface with corresponding retention features on the transmitter unit 104. The first retention feature 220A and the second retention feature 220B enable the transmitter unit 104 and the base unit 102 to be removably coupled together. Other numbers and types of retention feature and locations of retention features may be used. For example, the first retention feature 220A and the second retention feature 220B may include projections that engage with openings, slots, or other features in the transmitter unit 104. Optionally, magnets, Velcro, surfaces with adhesives, or the like may be used to allow detachment and/or attachment.

Figure 3:
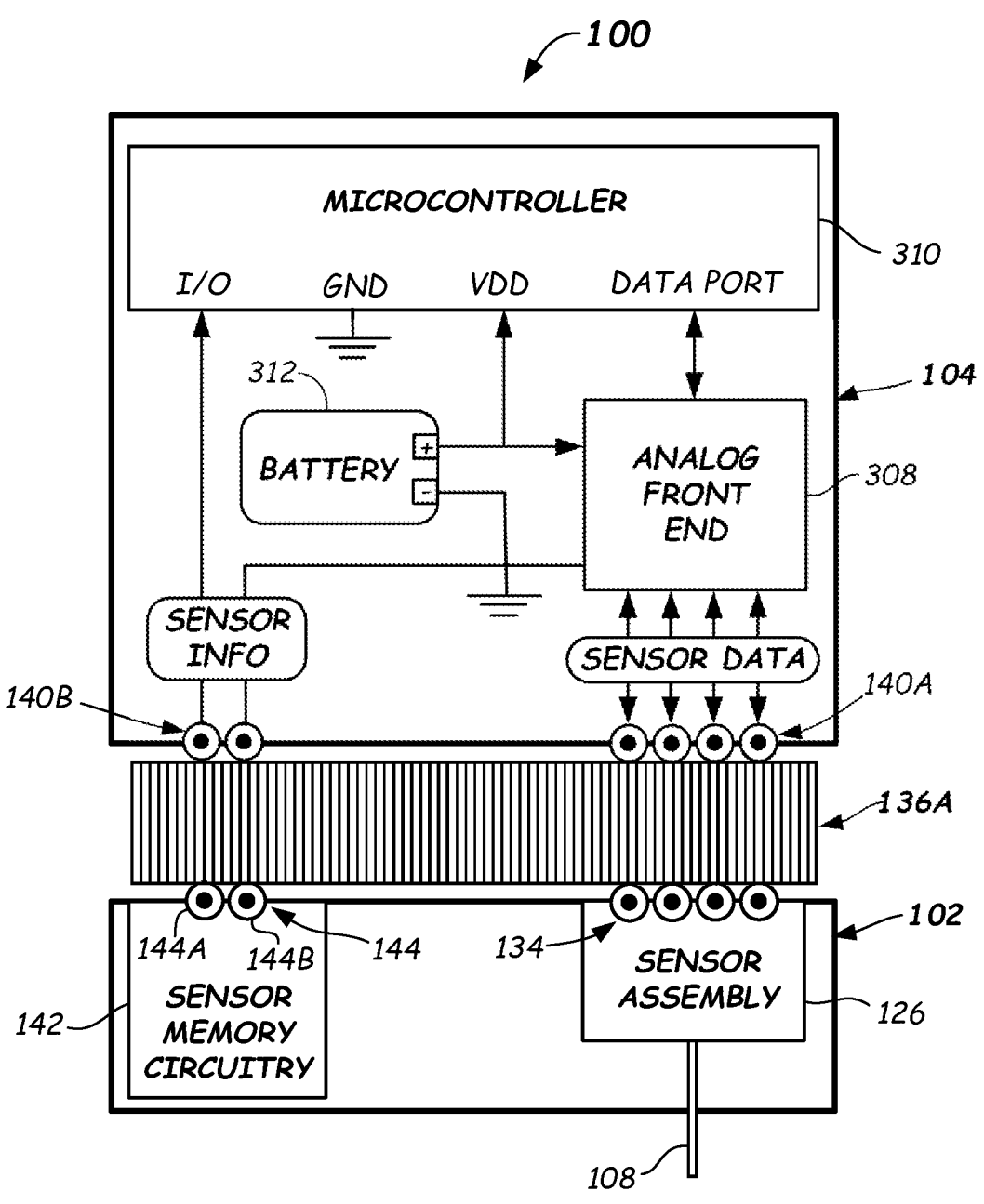
FIG. 3 illustrates a schematic diagram showing circuitry of the wearable device of FIG. 1C and connections there between in accordance with one or more embodiments provided herein.

Reference is now made to FIG. 3, which illustrates a schematic diagram of an embodiment of the wearable device 100. As shown in FIG. 3, electric signals may be transferred between the base unit 102 and the transmitter unit 104 via the connector 136 (or 136A) when the base unit 102 and the transmitter unit 104 are physically coupled together. For example, the contact pads 144 (e.g., the data contact pad 144A and the ground contact pad 144B) on the sensor memory circuitry 142 electrically couple with the memory pads 140B in the transmitter unit 104 by way of the connector 136. In a similar manner, the contact pads 134 on the sensor assembly 126 electrically couple with the sensor pads 140A in the transmitter unit 104. Thus, power and electronic signals may be transmitted between the transmitter unit 104 and the base unit 102 when the transmitter unit 104 and the base unit 102 are physically coupled together.

In some embodiments, the transmitter unit 104 may include an analog front end 308 that may be configured to drive the sensor assembly 126 and/or process sensor data generated by the sensor assembly 126 including the biosensor 108. The analog front end 308 may be configured to apply a bias voltage to the sensor assembly 126 and measure resulting current flow through the sensor assembly 126. For example, the analog front end 308 in conjunction with the sensor assembly 126 may apply the bias voltage to the biosensor 108 located in interstitial fluid and measure the resulting current. As described above, the resulting current is proportional to the analyte concentration. The analog front end 308 may perform other, fewer, and/or more functions.

The transmitter unit 104 may include a microcontroller 310 coupled to the analog front end 308 and/or other circuitry. The microcontroller 310 may include processing circuitry for processing sensor data generated by the sensor assembly 126 and/or the analog front end 308. For example, in some embodiments, the microcontroller 310 may convert analog current signals generated by the sensor assembly 126 to digital current signals, store current signals, and/or calculate analyte concentration levels based at least in part on the current signals. The microcontroller 310 may also communicate with the sensor memory circuitry 142 via an input/output (I/O) port. For example, the sensor information may be received via the I/O port.

In some embodiments, the microcontroller 310 may include a processor such as a microcontroller, a microprocessor, etc., processor memory, analog-to-digital converters, and the like. The processor memory may include computer program code stored therein that, when executed by the processor, causes the transmitter unit 104 and wearable device 100 to perform certain functions and/or communicate with one or more external devices, such as an external CGM device or a smart phone containing and capable of executing a software program (e.g., an application or an app) to calculate and/or display analyte data.

In some embodiments, the microcontroller 310 may transmit current signals, analyte concentration information, and/or other information to the external receiver device. In some embodiments, the microcontroller 310 may receive instructions, data, and/or other information from the external device.

The microcontroller 310 or other circuitry within the transmitter unit 104 may include circuitry configured to electrically couple to the sensor memory circuitry 142. In the embodiment of FIG. 3, the microcontroller 310 may include the input/output (I/O) port that electrically couples to the data contact pad 144A of the sensor memory circuitry 142 when the base unit 102 and the transmitter unit 104 are coupled together. The microcontroller 310 may receive data, such as the above-described sensor information related to one or more parameters of one or more components of the base unit 102, stored in the sensor memory circuitry 142 by way of the I/O port. In some embodiments, a signal (e.g., a pull signal) may be transmitted from the I/O port of the microcontroller 310 to the sensor memory circuitry 142 that causes the sensor memory circuitry 142 to transmit the data without user input. Thus, the sensor memory circuitry 142 may automatically transmit the data to the microcontroller 310 in response to the transmitter unit 104 and the base unit 102 being coupled together. Optionally, the transmission of the sensor information to the I/O port may be by way of a prompt, such as from the external device.

The microcontroller 310 may store the information transmitted from the sensor memory circuitry 142 and may use the information when calculating analyte concentrations and/or performing other functions. In other embodiments, the information may remain in the sensor memory circuitry 142 and may be accessed as needed by the microcontroller 310 or other circuitry during processing. As described above, the information stored in the sensor memory circuitry 142 may include sensor information related to sensitivity of the sensor assembly 126 and/or the biosensor 108, which may be used by the microcontroller 310 when calculating analyte concentrations based on measurements made by at least the sensor assembly 126 and/or the biosensor 108. In some embodiments, at least some of the information may be transmitted to the external device, which may use the information to calculate analyte concentrations. In some embodiments, the information may be provided to a user of the wearable device 100. For example, the date of manufacture and/or an expiration date of the base unit 102 may be provided to the user, which may enable the user to determine whether the base unit 102 should be used. In some embodiments, a security code matching a security code stored in the sensor memory circuitry 142 may need to be input by the user into the external device before communication can be initiated between the transmitter unit 104 and the base unit 102 or between the wearable device 100 and the external device.

The transmitter unit 104 may include a power source, such as a battery 312 that provides power to both the transmitter unit 104 and the base unit 102. In some embodiments, the power source may be located within the base unit 102 and in other embodiments, the base unit 102 and the transmitter unit 104 may each have their own power sources. In the embodiment of FIG. 3, the battery 312 may be located in the transmitter unit 104, so the base unit 102 does not need a power source. Accordingly, the cost of components and manufacturing of the base unit 102 is reduced relative to conventional devices. The battery 312 may provide power to the analog front end 308 and the microcontroller 310. When included on the transmitter unit 104, the battery may be rechargeable.

When the transmitter unit 104 and the base unit 102 are coupled together, the battery 312 may provide power to the sensor memory circuitry 142 and the sensor assembly 126, which, in some embodiments, may be provided via the analog front end 308. Examples of the battery 312 include flexible lithium polymer batteries, coin cell batteries such as lithium manganese, silver oxide, and alkaline coin batteries (e.g., CR 2032, SR516, and LR60 type coin batteries), or the like. Other power source/battery types may be used.

Figure 4A:
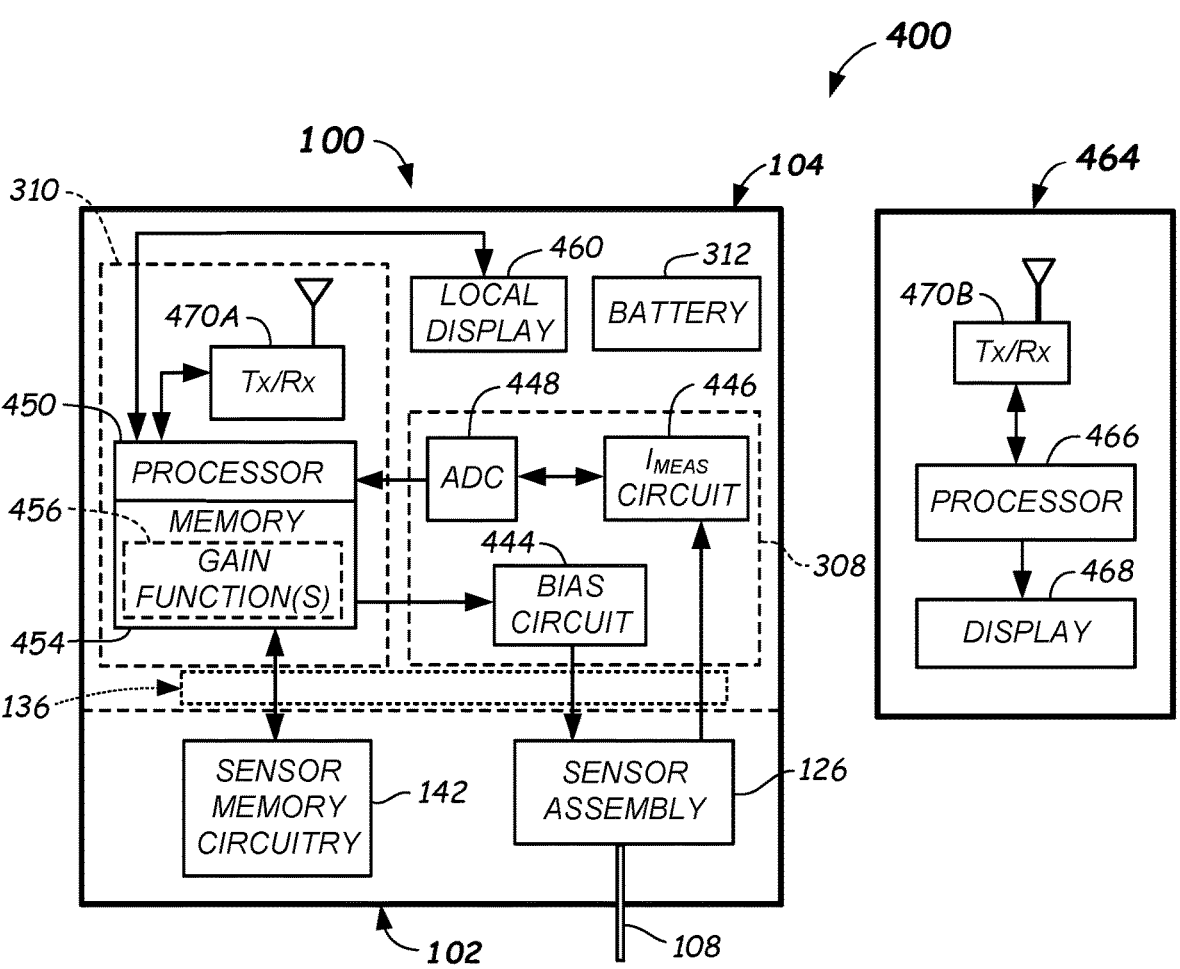
FIG. 4A illustrates a schematic diagram showing an analyte monitoring system including a wearable device and an external device in accordance with one or more embodiments provided herein.

FIG. 4A illustrates a more detailed block diagram of an example of an analyte monitoring system 400 in accordance with embodiments provided herein. In the embodiment of FIG. 4A, the analog front end 308 may include a bias circuit 444 that may be configured to couple to the sensor assembly 126 via the connector 136 (shown dotted, but may be as configured in FIG. 1C, 1D, or 2B). The bias circuit 444 may be configured to apply a bias voltage, such as a continuous DC bias voltage, to a sensor portion in contact with the analyte-containing fluid through the sensor assembly 126 and the biosensor 108. In this example embodiment, the analyte-containing fluid may be human interstitial fluid, and the bias voltage, for example, may be applied to electrodes (not shown) of the biosensor 108 (e.g., a working electrode, a counter electrode, etc.).

In some embodiments, the biosensor 108 may include at least two electrodes wherein the bias voltage may be applied across two of the electrodes. In such cases, the resulting current may be measured through the sensor assembly 126. In other embodiments, the biosensor 108 may include three electrodes such as a working electrode, a counter electrode, and a reference electrode. In such cases, the bias voltage may be applied between the working electrode and the reference electrode, and the resulting current may be measured through the working electrode, for example.

In the embodiments wherein the wearable device 100 is a continuous glucose monitor (CGM), the biosensor 108 and/ or electrodes thereof may include reagent chemicals that react with a glucose-containing solution in a reduction-oxidation reaction, which affects the concentration of charge carriers and the time-dependent impedance of the biosensor 108. Example chemicals include glucose oxidase, glucose dehydrogenase, or the like. In some embodiments, a mediator such as ferricyanide or ferrocene may be employed. In some embodiments, the biosensor 108 may include a micro-biosensor or a plurality of microbiosensors, such as a microbiosensor array.

The bias voltage generated and/or applied by the bias circuit 444 may range from about 0.1 to 1 volt relative to the reference electrode, for example. Other bias voltages may be used. Current passes through the biosensor 108 located in an analyte-containing fluid in response to the bias voltage and analyte concentrations in the analyte-containing fluid and are measured by a current measurement circuit 446 (also referred to as current sensing circuitry). The current measurement circuit 446 may be configured to sense and/or measure a current measurement signal ($I_{MEAS}$) that has a magnitude indicative of the magnitude of the current passing through the biosensor 108. In some embodiments, the current measurement circuit 446 may use a suitable current-to-voltage converter (CVC), for example. In some embodiments, the current measurement circuit 446 may include a resistor having a known nominal value and a known nominal precision (e.g., 0.1% to 5%, or even less than 0.1%, in some embodiments), through which the current conveyed from the biosensor 108 is passed. A voltage developed across the resistor of the current measurement circuit 446 represents the magnitude of the current and may be output as the current measurement signal ($I_{MEAS}$).

In some embodiments, a sampling circuit 448 may be coupled to the current measurement circuit 446 and may be configured to sample the current measurement signal $I_{MEAS}$. The sampling circuit 448 may produce digitized time-domain sample data that is representative of the current measurement signal $I_{MEAS}$ (e.g., digitized analyte (e.g., glucose) signals). For example, the sampling circuit 448 may be any suitable analog-to-digital converter (ADC) circuit configured to receive the current measurement signal $I_{MEAS}$, which, in this embodiment, is an analog signal, and convert it to a digital signal having a desired number of bits as an output. The number of bits output by sampling circuit 448 may be sixteen in some embodiments, but more or fewer bits may be used in other embodiments. In some embodiments, the sampling circuit 448 may sample the current measurement signal $I_{MEAS}$ at a sampling rate in the range of about 10 samples per second to 1,000 samples per second. Faster or slower sampling rates may be used. For example, sampling rates such as about 10 kHz to 100 kHz may be used and down-sampled to further reduce signal-to-noise ratio. Other suitable sampling circuitry may be employed.

The microcontroller 310 may include a processor 450 that may be coupled to the sampling circuit 448 and that may be further coupled to a memory 454. In some embodiments, the processor 450 and the sampling circuit 448 are configured to directly communicate with each other via a wired pathway (e.g., via a serial or parallel connection). In other embodiments, the coupling of the processor 450 and the sampling circuit 448 may be by way of the memory 454. In this configuration, the sampling circuit 448 writes data to the memory 454, and the processor 450 reads the data from the memory 454.

The memory 454 may have stored therein one or more gain functions 456 to be used in determining analyte levels (e.g., glucose levels) based on raw signals obtained from the current measurement circuit 446 and/or the sampling circuit 448. For example, in some embodiments, three or more gain functions may be stored in the memory 454, each for use with different segments (time periods) of analyte collected data. The memory 454 also may have stored therein a plurality of instructions that may, as an example, calculate analyte levels based in part on the current measurement signal $I_{MEAS}$ and the sensor information received from the sensor memory circuitry 142. In various embodiments, the processor 450 may be a computational resource such as, but not limited to, a microprocessor, a microcontroller, an embedded microcontroller, a digital signal processor (DSP), or a field programmable gate array (FPGA) configured to perform as a microcontroller, or the like.

The memory 454 may be memory such as, but not limited to, one or more of a volatile memory and/or a non-volatile memory. Volatile memory may include, but is not limited to, a static random access memory (SRAM), or a dynamic random access memory (DRAM). Non-volatile memory may include, but is not limited to, an electrically programmable read-only memory (EPROM), an electrically erasable programmable read-only memory (EEPROM), a flash memory (e.g., a type of EEPROM in either of the NOR or NAND configurations, and/or in either the stacked or planar arrangements, and/or in either the single-level cell (SLC), multi-level cell (MLC), or combination SLC/MLC arrangements), a resistive memory, a filamentary memory, a metal oxide memory, a phase change memory (such as a chalcogenide memory), or a magnetic memory. The memory 454 may be packaged as a single chip or as multiple chips, for example. In some embodiments, the memory 454 may be embedded, with one or more other circuits, in an integrated circuit, such as, for example, an application specific integrated circuit (ASIC). In some embodiments, the memory 454 may be integral with the processor 450.

In some embodiments, the plurality of instructions stored in the memory 454 may include instructions that, when executed by the processor 450, cause the processor 450 to: (a) receive sensor information stored in the sensor memory circuitry 142; (b) cause the wearable device 100 (via the bias circuit 444, the sensor assembly 126, the current measurement circuit 446 and/or the sampling circuit 448) to measure current signals from the biosensor 108; (c) store the current signals in the memory 454; (d) compute analyte levels (e.g., concentrations) based on the stored current signals, the gain functions 456, and/or the sensor information from the sensor memory circuitry 142; and (e) communicate the analyte levels to a user. In some embodiments the analyte levels are glucose levels, i.e., glucose concentrations.

As noted above, the memory 454 may have a plurality of instructions stored therein that, when executed by the processor 450, cause the processor 450 to perform various actions specified by one or more of the stored plurality of instructions. The memory 454 may further have portions reserved for one or more "scratchpad" storage regions that may be used for read or write operations by the processor 450 responsive to execution of one or more instructions of the plurality of instructions.

In the embodiment of FIG. 4A, the bias circuit 444, the sensor assembly 126, the current measurement circuit 446, the sampling circuit 448, the processor 450, and the memory 454, may be disposed within the transmitter unit 104 of the wearable device 100. In some embodiments, the transmitter unit 104 may include a local display 460 for displaying information such as analyte and/or glucose concentration information, without use of an external device. The local display 460 may be any suitable type of human-perceivable display, such as but not limited to, a liquid crystal display (LCD), a light-emitting diode (LED) display, or an organic light-emitting diode (OLED) display, and the like.

Still referring to FIG. 4A, the analyte monitoring system 400 may further include an external device 464 (e.g., an external receiver device). A processor 466 and a display 468 may be disposed within the external device 464. The display 468 may be coupled to the processor 466. The processor 466 may control the text or images shown by the display 468. In some embodiments, at least some of the sensor information stored in the sensor memory circuitry 142 may be transferred to the external device 464 where the sensor information may be processed by the processor 466 and displayed on the display 468. In some embodiments, at least some of the processing to determine analyte levels may be performed by the processor 466 and may be displayed on the display 468. The display 468 may be any suitable type of human-perceivable display, such as but not limited to, a liquid crystal display (LCD), a light-emitting diode (LED) display, or an organic light emitting diode (OLED) display, and the like.

The external device 464 and the transmitter unit 104 may be communicatively coupled. In some embodiments the communicative coupling of the external device 464 and the transmitter unit 104 may be by way of wireless communication via transmitter circuitry and/or receiver circuitry, such as a transmit/receive circuit 470A in the transmitter unit 104 and a transmit/receive circuit 470B in in the external device

464, for example. Such wireless communication may be by any suitable means including but not limited to standards-based communications protocols such as the Bluetooth® communications protocol. In various embodiments, wireless communication between the transmitter unit 104 and the external device 464 may alternatively be by way of near-field communication (NFC), radio frequency (RF) communication, infra-red (IR) communication, or optical communication. In some embodiments, the transmitter unit 104 and the external device 464 may be connected by one or more wires.

Figure 4B:
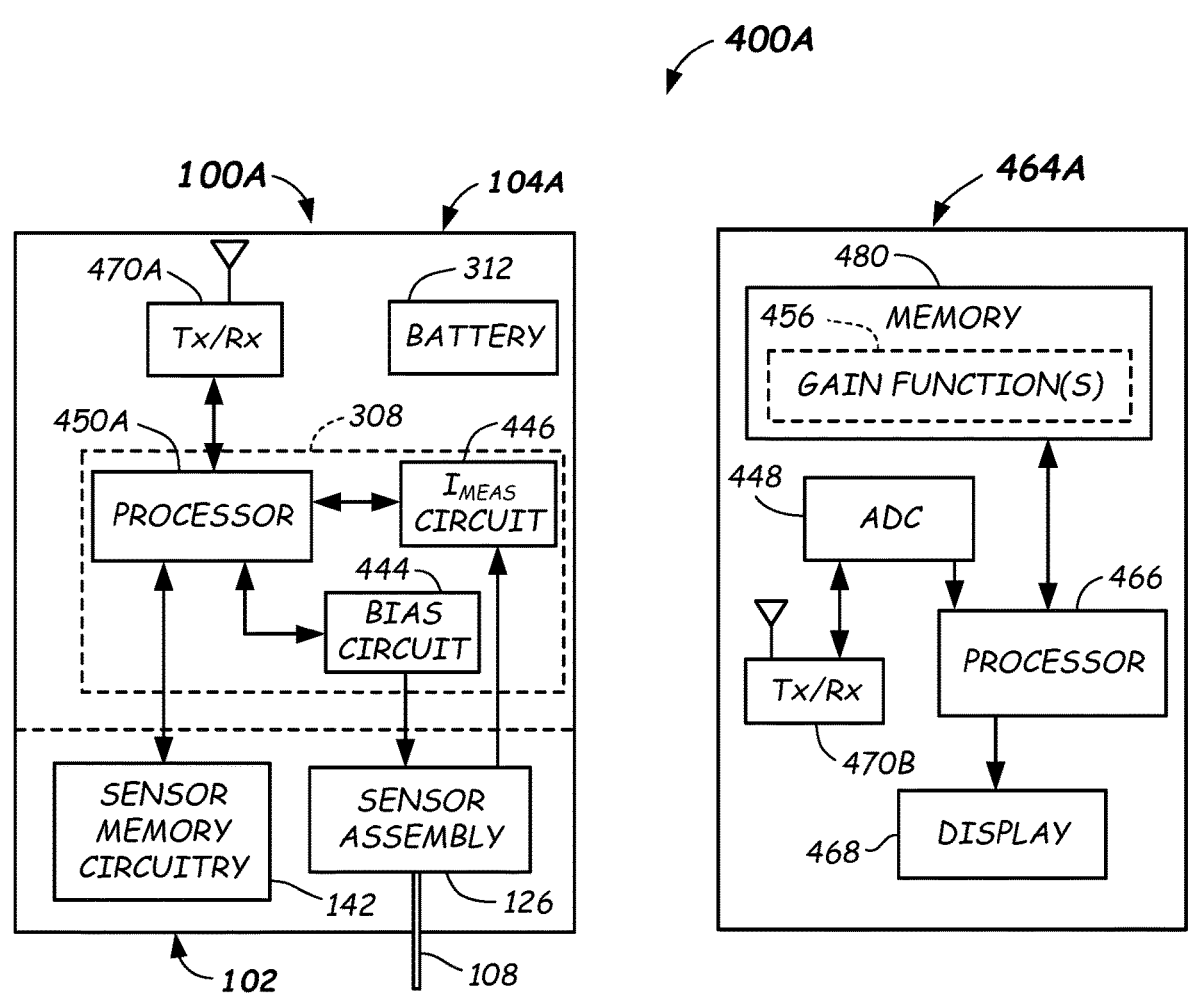
FIG. 4B illustrates a schematic diagram showing another analyte monitoring system including a wearable device and an external device in accordance with one or more embodiments provided herein.

Referring now to FIG. 4B, an example of an analyte monitoring system 400A is shown that is similar to the analyte monitoring system 400 illustrated in FIG. 4A, but having a different partitioning of components. In the analyte monitoring system 400A, the transmitter unit 104A includes the bias circuit 444 and the current measurement circuit 446 coupled to the sensor assembly 126. The transmitter unit 104A may include a processor 450A configured to transmit instructions to and/or from the bias circuit 444 and receive the current measurement signal $I_{MEAS}$ from the current measurement circuit 446. The processor 450A may also be configured to receive the information stored in the sensor memory circuitry 142 as described above. In addition, the processor 450A may be configured to receive and/or transmit data via the transmit/receive circuit 470A. The processor 450A in the transmitter unit 104A of the analyte monitoring system 400A may not perform all the functions of the processor 450 in the analyte monitoring system 400 of FIG. 4A.

The analyte monitoring system 400A may include an external device 464A (e.g., an external receiver device) that may perform more analysis than the external device 464 of the analyte monitoring system 400 of FIG. 4A. The analyte monitoring system 400A may function in a similar manner as the analyte monitoring system 400 of FIG. 4A with the exception that analyte concentration levels may be calculated in the external device 464A. In some embodiments, the external device 464A may include the sampling circuit 448 and the gain functions 456 that may be stored in a receiver memory 480. The processor 466 may be coupled to the receiver memory 480 and may receive the sensor information stored in the sensor memory circuitry 142 and may store the information in the receiver memory 480. The wearable device 100A of the analyte monitoring system 400A may be smaller and lighter, and therefore less invasive, than wearable device of FIG. 4A because sampling circuit 448 and the memory 454 are not included therein. Other component configurations may be employed. For example, as a variation to the transmitter unit 104 of FIG. 4B, the sampling circuit 448 may remain in the transmitter unit 104 such that external device 464A may receive current measurement signals $I_{MEAS}$ from the transmitter unit 104 in a digital format.

Figure 5:
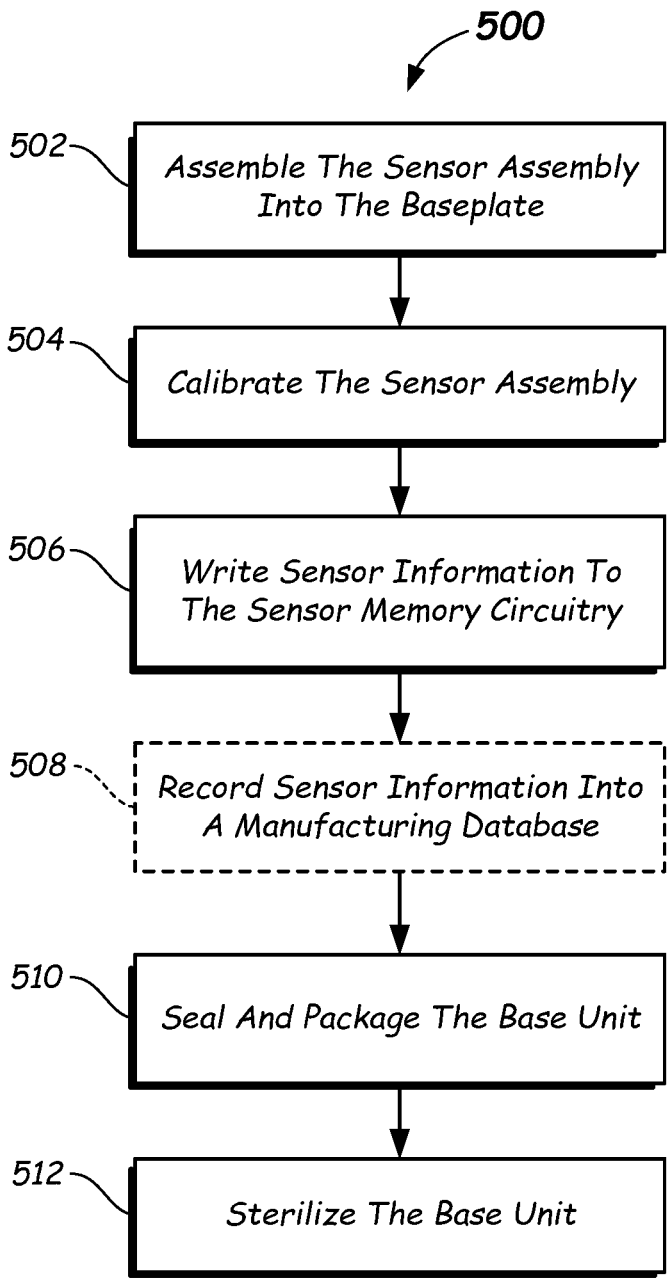
FIG. 5 is a flowchart of a method of manufacturing a base unit of a wearable device of a continuous analyte monitoring system in accordance with one or more embodiments provided herein.

FIG. 5 is a flowchart of an example of a method 500 of manufacturing the base unit 102 of the wearable device 100, 100A in accordance with embodiments provided herein. The method 500 begins in block 502 by assembling the sensor assembly 126 into the base unit 102. In some embodiments, the sensor memory circuitry 142 may be assembled to the base unit 102 at this time. In block 504, the sensor assembly 126 and other components of the base unit 102 may be calibrated. In some embodiments, the calibration may include measuring or calculating one or more parameters of the sensor assembly 126 and/or one or more other components of the base unit 102. For example, calibration may include measuring or calculating sensitivity parameters (e.g., one or more sensitivity slopes) of the biosensor 108 and/or other components of the sensor assembly 126. The sensitivity parameters may include one or more mathematical functions or one or more coefficients, for example, which may be obtained by testing the sensor assembly 126. Each biosensor and/or sensor assembly may be unique with regard to at least their sensitivities and other parameters.

In block 506, the calibration data and/or other data (sensor information) is written to the sensor memory circuitry 142. For example, a computer or similar device may be coupled to the contact pads 144 of the sensor memory circuitry 142 to write the information to the sensor memory circuitry 142. In some embodiments, the information stored on the sensor memory circuitry 142 may include a manufacturing date of the biosensor 108. In embodiments including more than one biosensor 108, the sensor information may include the date of manufacture of at least one of the biosensors. In some embodiments, the sensor information stored on the sensor memory circuitry 142 may include a manufacture date of one or more components of the base unit 102. In some embodiments, the sensor information stored on the sensor memory circuitry 142 may include at least one unique identifier of the one or more components of the base unit 102. The at least one unique identifier may include a lot number and/or a serial number, for example. In some embodiments, the sensor information stored on the sensor memory circuitry 142 may include a security code wherein the base unit 102 and/or components located thereon are only accessible by use of the security code. In some embodiments, the sensor information stored in the sensor memory circuitry 142 may include a sensor memory version of the sensor memory circuitry 142.

In some embodiments, the method 500 may optionally include block 508 wherein the sensor information stored in the sensor memory circuitry 142 is recorded and stored in a manufacturer database or another database. Accordingly, the manufacturer of the base unit 102 may access information pertaining to individual base units 102.

In block 510, the base unit 102 is sealed and packaged. For example, the base unit 102 may be sealed so as to prevent contaminants from entering the base unit 102. In some embodiments, the sealing may include making the base unit 102 waterproof. The base unit 102 may then be packaged in a package that may be sent to a user of the base unit 102. The base unit may be sterilized as described herein before or after being packaged. In some embodiments, the package may be hermetically sealed. Other methods of sealing the package may prevent contaminants, including biological material, from contacting the base unit 102. In block 512, the base unit 102 may be sterilized if it has not already been sterilized. In embodiments wherein the base unit 102 is in a package (e.g., sealed package), the base unit 102 may be sterilized while the base unit 102 is in the package. Sterilization may include exposing the base unit 102 to radiation. As described above, the sensor memory circuitry 142 may be rad-hard, so it is not damaged or erased when exposed to the radiation. In some embodiments, the packaging around the sensor memory circuitry 142 may provide the rad-hard capability.

In some embodiments, gamma ray or e-beam sterilization or another sterilization method may be employed to sterilize one or more components of the base unit 102, such as the sensor assembly 126 and/or the sensor memory circuitry 142. Example packaging may include a plastic housing having a removable plastic or foil seal, although any suitable packaging may be used.

The wearable device 100 may be employed by removing the sterilized base unit 102 from its sterile packaging, coupling the transmitter unit 104, 104A and the base unit 102 together, removing an adhesive strip from the second side 122B of the adhesive layer 122, and inserting the biosensor 108 into a user using an insertion device (not shown) while attaching the base unit 102 to the skin surface 118S of the user. Any suitable insertion device may be employed for inserting the biosensor 108 into an interstitial fluid region of the user.

Figure 6:
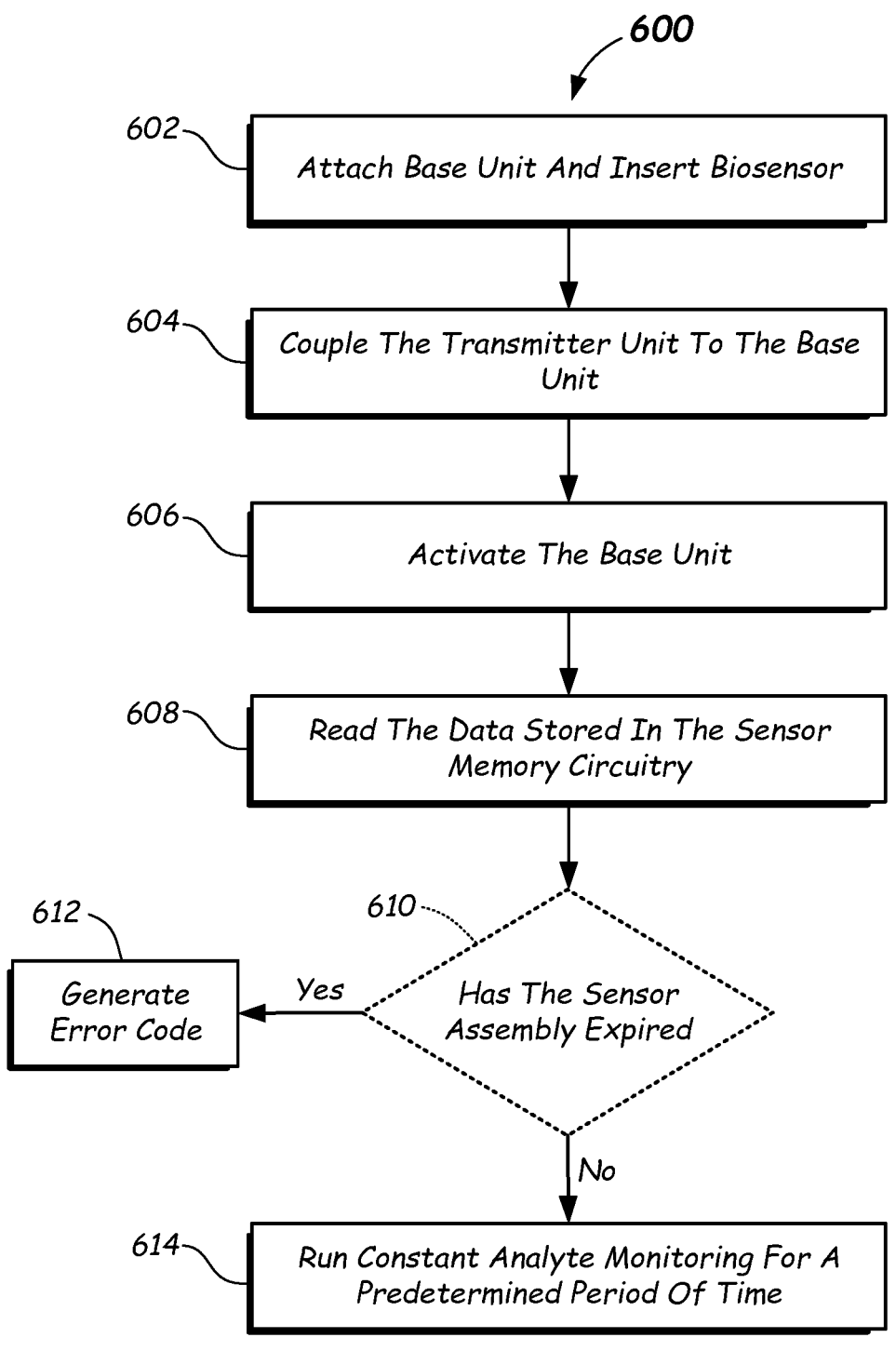
FIG. 6 is a flowchart of a method of continuous analyte monitoring using a wearable device including a base unit and a transmitter unit in accordance with one or more embodiments provided herein.

Reference is now made to FIG. 6, which is a flowchart of an example of a method 600 for continuous analyte monitoring in accordance with embodiments provided herein. The method 600 begins in block 602 in which the base unit 102 having the sensor assembly 126 and sensor memory circuitry 142 located therein is attached to a skin surface 118S of a user. The biosensor 108 is inserted into an interstitial fluid region and the base unit 102 may be attached to the user via the adhesive layer 122 attached to the second surface 110B of the baseplate 110. For example, the second side 122B of the adhesive layer 122 may be adhered to the skin surface 118S of the user so that the base unit 102 is adhered to the skin surface 118S.

In block 604, the transmitter unit 104 is coupled to the base unit 102. In block 606, the base unit 102 is activated. For example, power may be applied to the sensor assembly 126 and/or the sensor memory circuitry 142 by way of the battery 312. In embodiments wherein the battery 312 is located in the transmitter unit 104, the base unit 102 may be activated when the base unit 102 and the transmitter unit 104 are coupled together. In embodiments wherein the battery is located in the base unit 102, the coupling of the transmitter unit 104 and the base unit 102 together may cause the battery to activate the base unit 102. Other suitable forms of activation may be used, such as receiving a prompt or signal from the external device 464, 464A.

In block 608, the sensor information stored in the sensor memory circuitry 142 is read or otherwise output. In some embodiments, the sensor memory circuitry 142 may output the information upon activation of the base unit 102 in block 606. In the embodiment of FIG. 4A, sensor information related to processing the current measurement signal $I_{MEAS}$ and the gain functions 456 may be output to the memory 454 in the transmitter unit 104 where the analyte concentration may be at least partially calculated. In the embodiment of FIG. 4B, the gain functions 456 may be output to the processor 466 in the external device 464A. Other sensor information, such as manufacture dates, model numbers, and the like may be processed and displayable on the local display 460 and/or the display 468.

Decision block 610 shows an optional inquiry that may be made regarding the sensor information. In decision block 610 a determination is made as to whether the sensor assembly 126 has expired. For example, a determination may be made as to whether the period between the date of manufacture of the sensor assembly 126 and the present date is greater than a predetermined period. If the sensor assembly 126 has expired, processing may proceed to block 612 where an error code can be generated. The error code may indicate that the sensor assembly 126 has expired. As described herein, other error codes may be displayed in block 612.

In some embodiments, the sensor information may include the model number of the base unit 102 as described above and a decision block may determine if the base unit 102 is the correct model. If the base unit 102 is not the correct model, block 612 may generate an error code. In some embodiments, the sensor information may include a security code as described above. A decision block may compare the security code with a known code, such as a code stored in the memory 454 and/or the receiver memory 480 and/or a code entered by a user. If the security code and the other code do not match, an error code may be generated. The security code may prevent bootleg or unauthorized base units from being used in the wearable device 100.

If the outcome of decision block 610 is negative (No), processing may proceed to block 614 where the transmitter unit 104, 104A and the base unit 102 are employed to monitor analyte levels within the user for a first predetermined time period. The running of the analyte monitoring may be constant, i.e., meaning sensing continuously over the predetermined period at a predetermined rate or as dictated by the user. For example, the transmitter unit 104, 104A and base unit 102 may be used to monitor glucose or other analyte(s) levels for 7, 10, 14 or another number of days. At the expiration of the time period, the base unit 102 may be replaced with a new base unit. The sensor information stored in the new base unit may be read and may replace sensor information from the previous base unit 102. Thus, processing of analyte levels will be based on calibration information and sensor information specific to the new base unit 102.

The wearable devices described herein may be used to monitor analyte concentrations of any desired analyte. Example analytes that may be detected and/or monitored include glucose, cholesterol, lactate, uric acid, alcohol, or the like. In some embodiments, the sensor assembly 126 and/or the biosensor 108 may be continuously operated at a constant potential against a reference electrode, such as an Ag/AgCl electrode, or a combined reference-counter electrode. The sensor assembly 126 and/or the biosensor 108 may also be operated with two working electrodes where one is dedicated to measuring a point-of-interest analyte, such as glucose, by a glucose specific enzyme such as glucose oxidase. The other electrode is dedicated to measuring the background signals that result from interference species such as uric acid, acetaminophen, or the like. In this dual electrode operation scheme, the interference signal may be constantly subtracted from the main signal of the point-of-interest analyte by either simple subtraction or another algorithmic method.

While the transmitter units 104, 104A are shown as being removable and/or attachable to the top surface of the base unit 102, it will be understood that in other embodiments, the transmitter units 104, 104A may be removable and/or insertable into other surfaces or areas of the base unit 102. For example, the base unit 102 may have an opening that allows the transmitter unit 104 to be inserted in or removed from the bottom or a side of the base unit 102 in accordance with some embodiments. In other embodiments, the base unit 102 may include an opening configured to receive the transmitter unit 104. In such embodiments, a recess may be formed for a cover to cover the opening including the transmitter unit 104.

Figure 7:
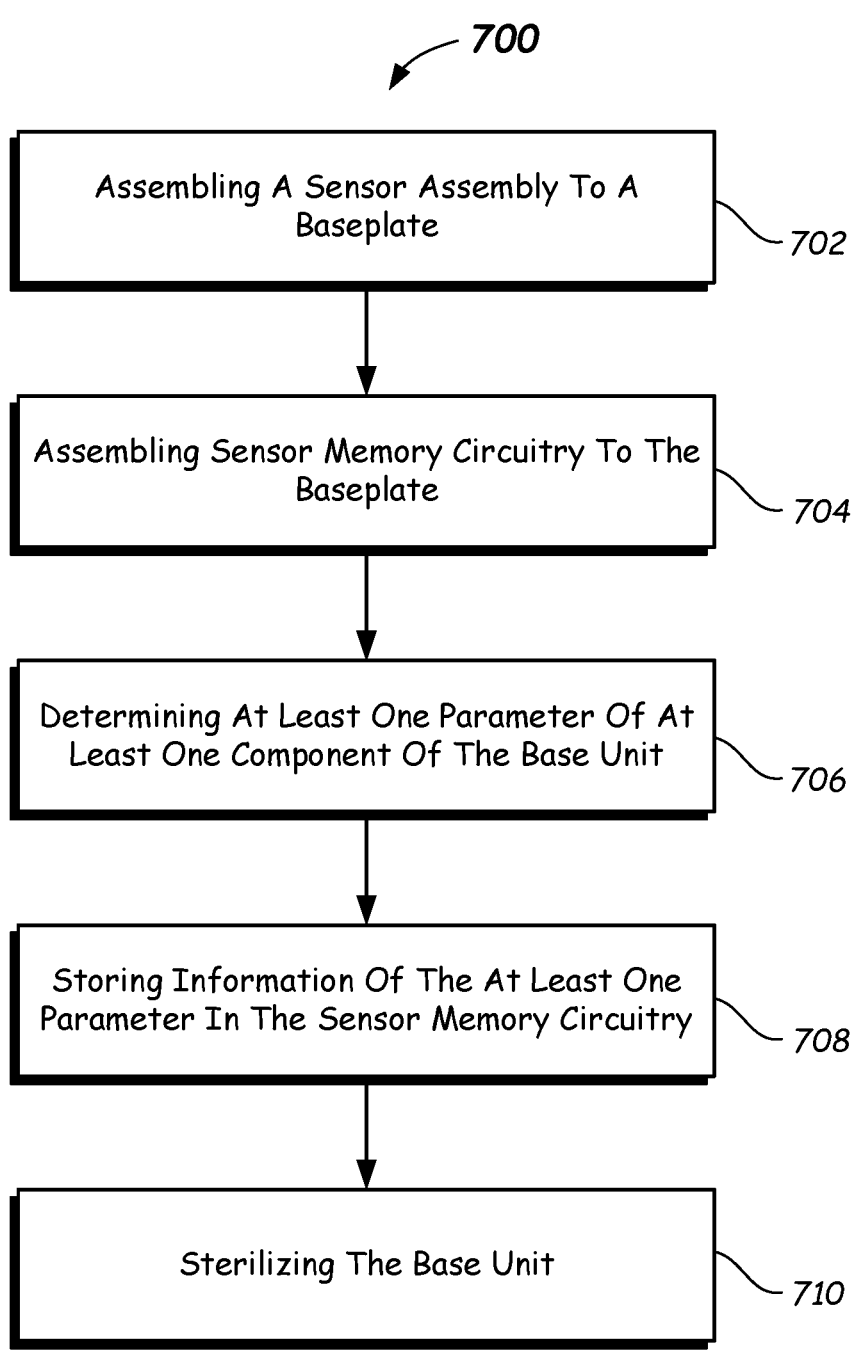
FIG. 7 is a flowchart of a method of manufacturing a base unit of a constant analyte monitor in accordance with one or more embodiments provided herein.

Reference is now made to FIG. 7, which is a flowchart illustrating a method 700 of manufacturing a base unit (e.g., base unit 102) of a constant analyte monitor (e.g., wearable device 100). The method 700 includes, in block 702, assembling a sensor assembly (e.g., sensor assembly 126) to a baseplate (e.g., baseplate 110). The method 700 also includes, in block 704, assembling sensor memory circuitry (e.g., sensor memory circuitry 142) to the baseplate. The method further includes, in block 706, determining at least one parameter of at least one component of the base unit. The method 700 also includes, in block 708, storing information of the at least one parameter in the sensor memory circuitry. In some embodiments, the method 700 includes, in block 710, sterilizing the base unit.

Figure 8:
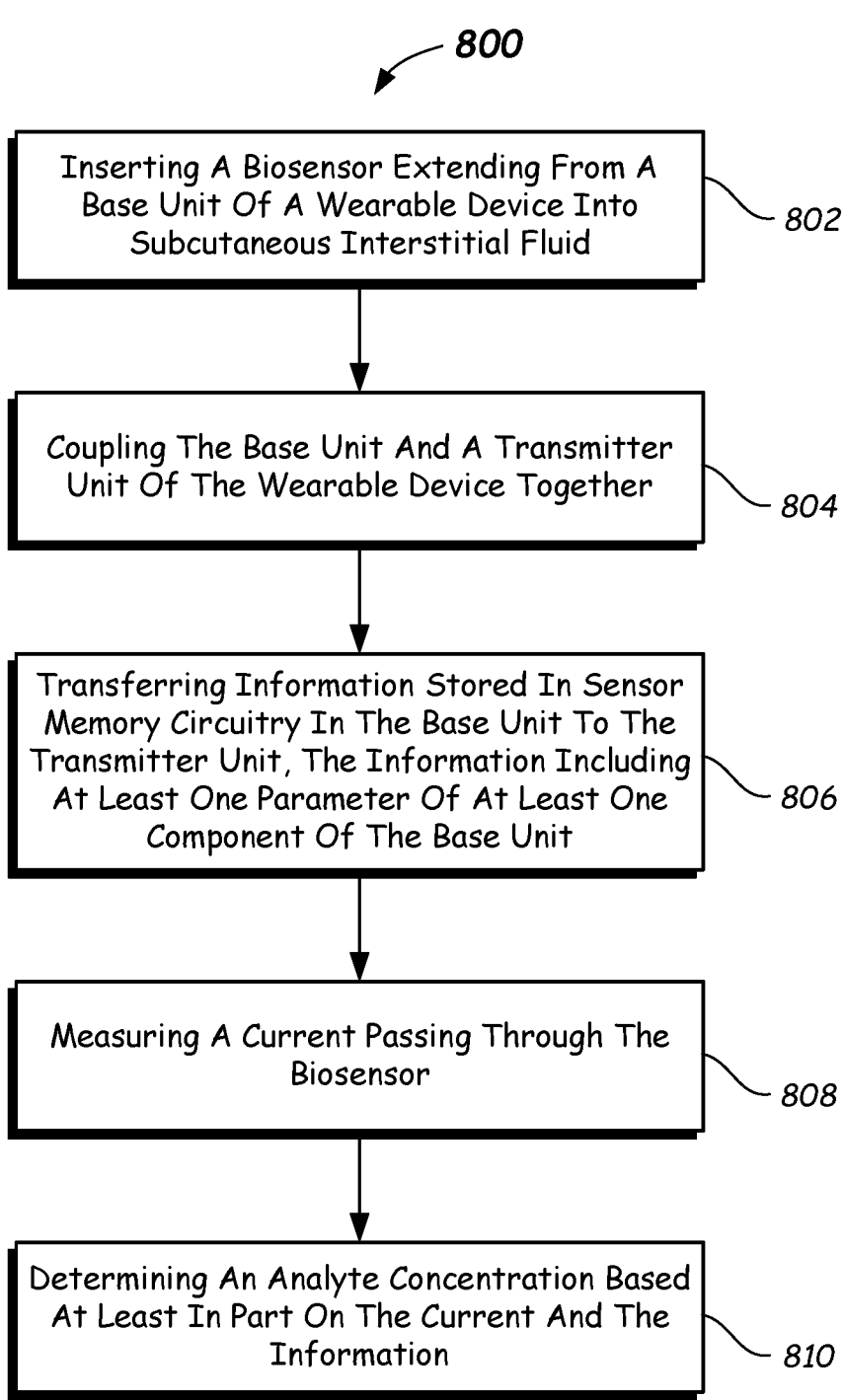
FIG. 8 is a flowchart of a method of monitoring analytes subcutaneously in accordance with one or more embodiments provided herein.

Reference is now made to FIG. 8, which is a flowchart illustrating a method 800 of monitoring analytes subcutaneously. The method 800 includes, in block 802, inserting a biosensor (e.g., biosensor 108) extending from a base unit (e.g., base unit 102) of a wearable device (e.g., wearable device 100) into subcutaneous interstitial fluid. The method 800 also includes, in block 804, coupling the base unit and a transmitter unit (e.g., transmitter unit 104) of the wearable device together. The method 800 further includes, in block 806, transferring information stored in sensor memory circuitry (e.g., sensor memory circuitry 142) in the base unit to the transmitter unit, the information including at least one parameter of at least one component of the base unit. The method 800 also includes, in block 808, measuring a current passing through the biosensor. The method 800 further includes, in block 810, determining an analyte concentration based at least in part on the current and the information.

Embodiments provided herein allow for flexible and ultra-low profile wearable units. In some embodiments, the height of the wearable unit may be less than about 2.5 mm. This reduction in overall height may reduce interfere with clothing, be more discreet, and may improve overall comfort for wearers of the wearable unit. The flexible construction and components allow the wearable unit to be contoured to a user's body through a range of motions and serves to increase overall user comfort. Critical components can be supported by rigid stiffeners in specific locations while maintaining overall flexibility.

The wearable devices described herein further enable accurate analyte monitoring using a transmitter unit 104, 104A coupled to a plurality of different base units 102 over the life of the transmitter unit. By storing information unique to one or more parameters of one or more components of the individual base units, accurate analyte monitoring is achieved irrespective of the base unit coupled to the transmitter unit.

In some embodiments, the materials used (e.g., LSR), flexible circuit boards (e.g., substrate 152—FIG. 1), etc., provide a wearable device 100 that may be worn comfortably under clothing, has a low profile and avoid impacts, presents a soft flexible feel and appearance, and contours and moves with the dynamics of tissue flex, expansion, and contraction. The disclosed devices also may protect sensor sites and internal hardware from fluid ingress and other use hazards, are applied easily and comfortably, provide breathability/air flow at skin adhesive areas, and create a generally more user-friendly experience.

The foregoing description discloses only example embodiments. Modifications of the above-disclosed apparatus and methods which fall within the scope of this disclosure will be readily apparent to those of ordinary skill in the art.

What is claimed is:

1. A wearable device configured for use during continuous analyte monitoring, comprising:
    a base unit, comprising:
        a sensor assembly including at least one biosensor configured to be located subcutaneously; and
        radiation hardened sensor memory circuitry configured to store information related
            to at least one parameter of at least one component of the base unit; wherein:
            the at least one component includes the at least one biosensor, the at least one parameter includes a sensitivity slope for the at least one biosensor, the information is transferable to a transmitter unit automatically, via a pull signal, in response to a physical coupling of the base unit and the transmitter unit, a power source located in the base unit, and the radiation hardened sensor memory circuitry comprises:

a data contact pad for transferring the information to the transmitter unit; and a radiation hardened memory such that the radiation hardened memory stores the information and retains the information when exposed to radiation used to sterilize the base unit; and a connector electrically coupled to the data contact pad and configured to electrically couple the radiation hardened sensor memory circuitry to the transmitter unit, wherein the connector comprises at least one electrode that is axially moveable within a body of the connector and biased in a direction of the transmitter unit relative to the base unit to make electrical contact with a memory pad within the transmitter unit, wherein the data contact pad is configured to electrically couple to the memory pad of the transmitter unit via the connector;

the transmitter unit, comprising:

one or more components configured to receive the information stored in the radiation hardened sensor memory circuitry of the base unit of the wearable device automatically, without user input, in response to the transmitter unit and the base unit being physically coupled, wherein the information includes the at least one parameter of the at least one component of the base unit, wherein the transmitter unit does not include the power source; and wherein the one or more components includes a microcontroller that, upon the physical coupling of the base unit and the transmitter unit, electrically couples to the data contact pad of the radiation hardened sensor memory circuitry via the connector and generates the pull signal that automatically initiates a transfer of the information from the base unit to the transmitter unit, without the user input.

2. The wearable device of claim 1, wherein the microcontroller uses the sensitivity slope for the at least one biosensor to calculate an analyte concentration.

3. The wearable device of claim 1, wherein the at least one parameter further includes at least one parameter selected from the group consisting of:

a manufacturing date of the at least one component in the base unit, a manufacturing date of the base unit, at least one unique identifier of the at least one component of the base unit, a security code operable to enable the transmitter unit to function with the base unit, a version of the radiation hardened sensor memory circuitry, and a serial number of the at least one component of the base unit.

4. The wearable device of claim 1, further comprising a connector configured to electrically couple the sensor assembly to at least one component in the transmitter unit in response to the base unit and the transmitter unit being coupled together.

5. The wearable device of claim 1, wherein the power source is a first power source, and wherein at least one of the sensor assembly and the radiation hardened sensor memory circuitry is configured to be powered by a second power source located in the transmitter unit.

6. The wearable device of claim 1, wherein at least one of the sensor assembly and the radiation hardened sensor memory circuitry are configured to receive power in response to the base unit and the transmitter unit being coupled together.

7. The wearable device of claim 1, wherein the base unit is sterilized by exposure to radiation.

8. The wearable device of claim 1, wherein the at least one biosensor is configured to measure glucose.

9. The wearable device of claim 1, wherein the radiation hardened sensor memory circuitry further comprises a ground contact pad.

10. The wearable device of claim 1, wherein the at least one biosensor comprises a plurality of biosensors configured to be located subcutaneously, and wherein the at least one parameter includes one or more sensitivity slopes of each of the plurality of biosensors.

11. The wearable device of claim 1, wherein the pull signal causes the radiation hardened sensor memory circuitry to transmit the at least one parameter to the microcontroller.

12. The wearable device of claim 1, wherein the one or more components of the transmitter unit are configured to be reusable with an additional base unit for receiving information stored in the additional base unit.

13. A wearable device for use during continuous analyte monitoring, comprising:

a transmitter unit;

a base unit, comprising:

a power source;

radiation hardened sensor memory circuitry comprising a radiation hardened memory that stores information and retains the information when exposed to radiation used to sterilize the base unit, wherein the information includes at least one parameter of at least one component of the base unit, wherein the at least one parameter comprises at least one sensitivity slope for at least one biosensor of the base unit, wherein the radiation hardened sensor memory circuitry comprises a data contact pad; and a connector electrically coupled to the data contact pad and configured to electrically couple the radiation hardened sensor memory circuitry to the transmitter unit, wherein the connector comprises at least one electrode that is axially moveable within a body of the connector and biased in a direction of the transmitter unit relative to the base unit to make electrical contact with a memory pad within the transmitter unit, wherein the data contact pad is configured to electrically couple to the memory pad of the transmitter unit via the connector; and the transmitter unit, comprising:

one or more components configured to automatically, without user input, receive the information stored in the radiation hardened sensor memory circuitry of the base unit in response to the transmitter unit and the base unit being physically coupled together, wherein the one or more components includes a microcontroller that electrically couples to the data contact pad when the base unit and the transmitter unit are physically coupled, wherein the data contact pad is configured to transfer the information to the microcontroller, wherein the microcontroller, in response to the transmitter unit and the base unit being physically coupled together, electrically couples to the data contact pad of the radiation hardened sensor memory circuitry and generates a pull signal that automatically initiates a transfer of the information from the base unit to the transmitter unit, without the user input.

14. The wearable device of claim 13, wherein the at least one parameter further includes at least one parameter selected from the group consisting of:

a manufacturing date of the at least one component in the base unit, a manufacturing date of the base unit, at least one unique identifier of the at least one component of the base unit, a security code, a version of the radiation hardened sensor memory circuitry, and a serial number of the at least one component of the base unit.

15. The wearable device of claim 13, wherein the radiation used to sterilize the base unit is at least one of a gamma radiation or an electron beam radiation.

16. The wearable device of claim 13, wherein the transmitter unit does not include the power source.

17. A method of manufacturing a base unit of a continuous analyte monitor, comprising:

assembling a sensor assembly to a baseplate, the sensor assembly comprising one or more biosensors configured to be located subcutaneously;

assembling radiation hardened sensor memory circuitry to the baseplate, the radiation hardened sensor memory circuitry comprising:

a data contact pad; and a radiation hardened memory such that the radiation hardened memory stores information related to at least one parameter of at least one component of the base unit and retains the information when exposed to radiation used to sterilize the base unit; and a connector electrically coupled to the data contact pad and configured to electrically couple the radiation hardened sensor memory circuitry to a transmitter unit of the continuous analyte monitor, wherein the connector comprises at least one electrode that is axially moveable within a body of the connector and biased in a direction of the transmitter unit relative to the base unit to make electrical contact with a memory pad within the transmitter unit, wherein the data contact pad is configured to electrically couple to the memory pad of the transmitter unit via the connector;

determining the at least one parameter of the at least one component of the base unit, wherein the at least one parameter comprises at least one sensitivity slope for each of the one or more biosensors, and wherein the at least one sensitivity slope is stored in the radiation hardened memory; and storing the information of the at least one parameter in the radiation hardened memory, wherein the at least one sensitivity slope is configured to be transmitted to the transmitter unit of the continuous analyte monitor automatically, without user input, when the base unit and the transmitter unit are physically coupled, wherein the at least one sensitivity slope is transferred from the data contact pad configured to be electrically connected to a microcontroller of the transmitter unit, wherein the microcontroller, in response to the transmitter unit and the base unit being physically coupled, electrically couples to the data contact pad of the radiation hardened sensor memory circuitry and generates a pull signal that automatically initiates a transfer of the information from the base unit to the transmitter unit, without the user input, wherein a power source is located in the base unit.

18. The method of claim 17, wherein the determining the at least one parameter further includes determining at least one parameter selected from the group consisting of:

a manufacturing date of the at least one component in the base unit, a manufacturing date of the base unit, at least one unique identifier of the at least one component in the base unit, a security code, a version of the radiation hardened sensor memory circuitry, and a serial number of the at least one component in the base unit.

19. The method of claim 17, wherein the transmitter unit does not include the power source.

20. A method of monitoring analytes subcutaneously, comprising:

inserting a biosensor extending from a base unit of a wearable device into subcutaneous interstitial fluid;

physically coupling the base unit and a transmitter unit of the wearable device together;

responsive to physically coupling the base unit and the transmitter unit, automatically, without user input, transferring information stored in radiation hardened sensor memory circuitry in the base unit to the transmitter unit, the information including at least one parameter of at least one component of the base unit, wherein the radiation hardened sensor memory circuitry comprises a radiation hardened memory that stores the information and retains the information when exposed to radiation used to sterilize the base unit, wherein the radiation hardened sensor memory circuitry of the base unit comprises a data contact pad configured to electrically couple to a microcontroller of the transmitter unit, and wherein the at least one parameter comprises a first sensitivity slope for the biosensor;

measuring a current passing through the biosensor;

determining an analyte concentration based at least in part on the current and the information, wherein the microcontroller electrically couples to the data contact pad of the radiation hardened sensor memory circuitry via a connector of the base unit and generates a pull signal that automatically initiates a transfer of the information from the base unit to the transmitter unit, without the user input, wherein the connector comprises at least one electrode that is axially moveable within a body of the connector and biased in a direction of the transmitter unit relative to the base unit to make electrical contact with a memory pad within the transmitter unit, wherein the data contact pad is configured to electrically couple to the memory pad of the transmitter unit via the connector;

wherein a power source is located in the base unit, and wherein the transmitter unit does not include the power source.

21. The method of claim 20, further comprising:

responsive to a determination that the at least one component of the base unit has expired, causing generation of an error code.

22. The method of claim 21, further comprising:

providing an additional base unit, the additional base unit storing an additional sensitivity slope for an additional biosensor of the additional base unit, wherein the additional sensitivity slope is distinct from the first sensitivity slope.

23. The method of claim 22, further comprising:

physically coupling the additional base unit to the transmitter unit; and determining an additional analyte concentration based on the additional sensitivity slope.

* * * * *